United States Patent [19]

Penney et al.

[11] Patent Number: 5,258,791
[45] Date of Patent: Nov. 2, 1993

[54] SPATIALLY RESOLVED OBJECTIVE AUTOREFRACTOMETER

[75] Inventors: Carl M. Penney, Saratoga Springs, N.Y.; Robert H. Webb, Lincoln, Mass.; Jerome J. Tiemann, Schenectady, N.Y.; Keith P. Thompson, Atlanta, Ga.

[73] Assignee: General Electric Company, Schenectady, N.Y.

[21] Appl. No.: 557,263

[22] Filed: Jul. 24, 1990

[51] Int. Cl.⁵ ............................ A61B 3/10; A61B 3/14
[52] U.S. Cl. ................................... 351/211; 351/208
[58] Field of Search ............... 351/205, 206, 211, 221, 351/208

[56] References Cited

U.S. PATENT DOCUMENTS

| | | |
|---|---|---|
| 3,524,702 | 8/1970 | Bellows .................. 351/211 |
| 4,213,678 | 7/1980 | Pomerantzeff ............ 351/221 |
| 4,421,391 | 12/1983 | Matsumura ............... 351/211 |
| 4,435,051 | 3/1984 | Nunokawa ............... 351/208 |
| 4,665,913 | 5/1987 | L'Esperance, Jr. . |
| 4,669,466 | 1/1987 | L'Esperance, Jr. . |
| 4,702,596 | 10/1987 | Nahda .................. 351/211 |
| 4,781,453 | 11/1988 | Kobayashi ............ 351/221 X |
| 4,838,679 | 6/1989 | Bille ................ 351/221 X |
| 4,854,691 | 8/1989 | Sekine et al. ........... 351/221 |
| 4,923,467 | 5/1990 | Thompson . |

Primary Examiner—Rodney B. Bovernick
Attorney, Agent, or Firm—James R. McDaniel; Paul R. Webb, II

[57] ABSTRACT

A spatially resolved map of the eye's refractive characteristics are provided by measuring the eye's refractive characteristics on a point-by-point basis across the anterior surface of the eye. This spatially resolved refraction data may be obtained subjectively by providing a reference pattern and a measurement beam, by establishing a particular position on the cornea as the location to be measured and manipulating the orientation of the measurement beam at that measurement point to bring the measurement beam to a desired position relative to the reference image. When the patient indicates that the measurement beam is in the desired position relative to the reference pattern, the orientation of the beam is recorded as the refractive data for that measurement point and the process proceeds to another measurement point. This provides relatively rapid, physiologically accurate refractive data on a spatially resolved basis. Alternatively, this spatially resolved refraction data may be obtained objectively by independently controlling the position and orientation of a measurement beam and using a feedback null system to determine the refractive characteristics. This enables rapid, automatic non-subjective determination of the refractive characteristics of the eye and thereby provides the ability to provide improved correction of the eye. This spatially resolved refraction information enables spatially resolved correction of vision by spatially resolved shaping of the anterior surface of the eye.

36 Claims, 13 Drawing Sheets

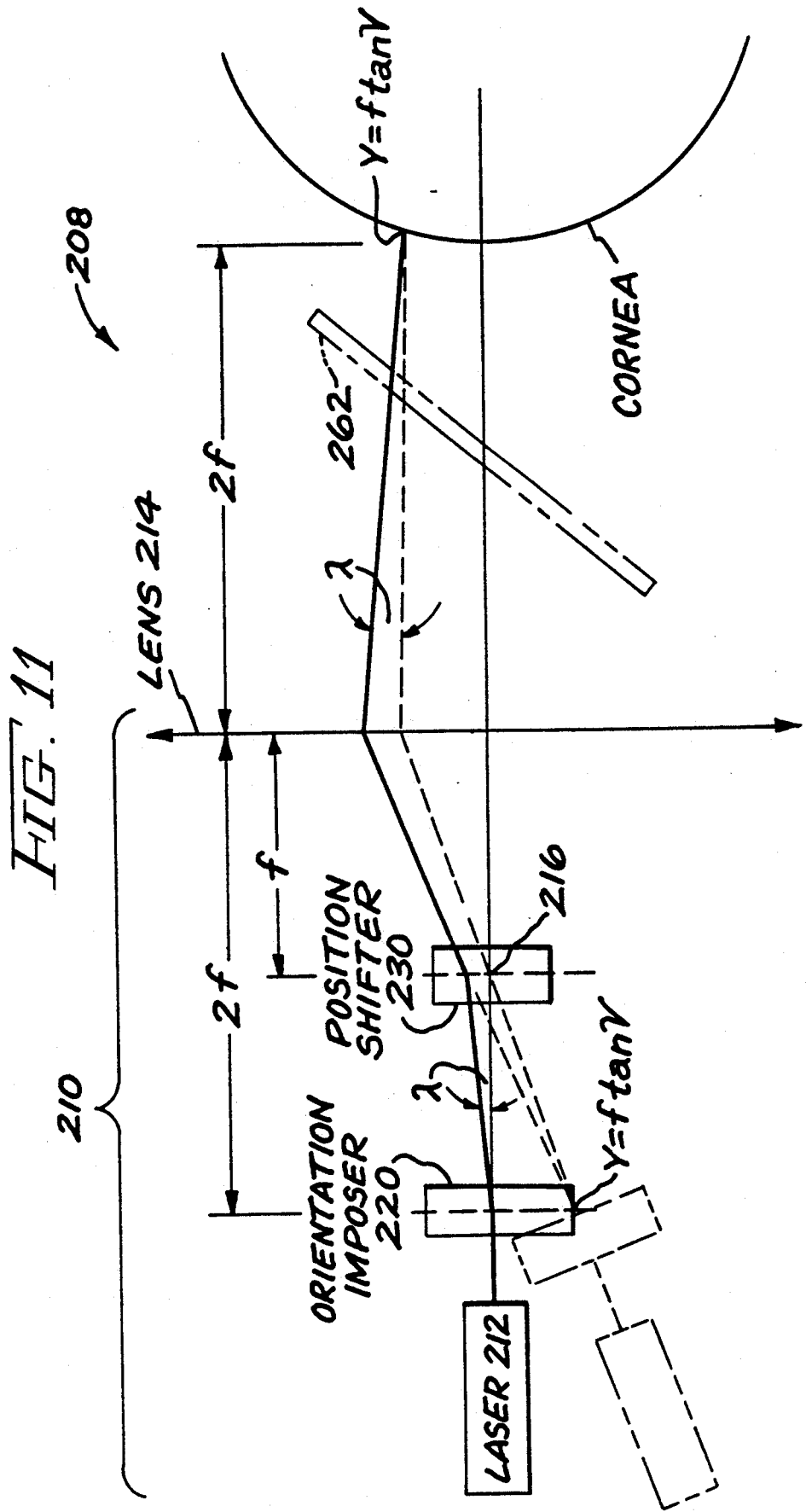

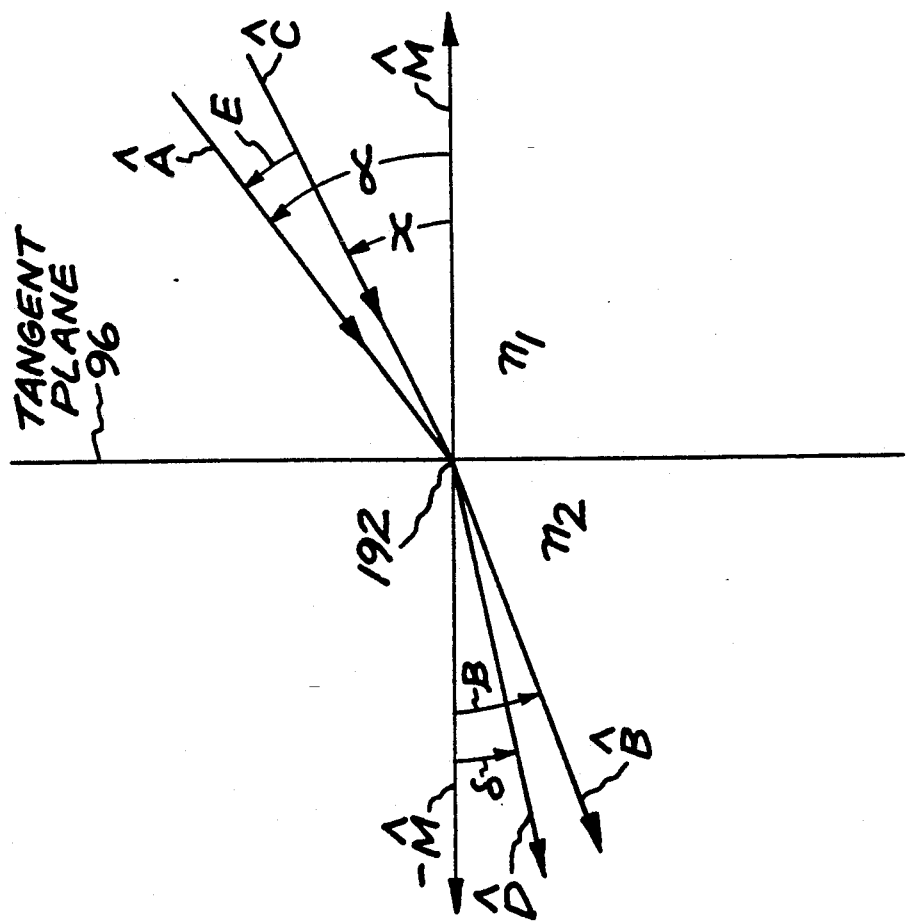

SPATIALLY RESOLVED OBJECTIVE AUTOREFRACTOMETER

RELATED APPLICATION

This application is related to U.S. patent application Ser. No. 07/402,946, filed Sep. 5, 1989 and entitled, "Laser Shaping With an Area Patterning Mask" by R. M. Levinson et al. now abandoned, which is incorporated herein by reference in its entirety.

BACKGROUND OF THE INVENTION

1. Field of the Invention

The present invention relates to the field of measurement of the refractive characteristics of an optical system, and more particularly, to automatic measurement of the refractive characteristics of the human or other animal eye and to corrections to the vision thereof.

2. Background Information

The refractive characteristics of individual components of such man-made optical systems as telescopes, microscopes, cameras and so forth are well understood and susceptible to accurate, non-subjective measurement as are the overall characteristics of such systems.

In such optical systems, prior to their assembly, each component of the optical system is individually accessible for shaping, measurement, modification, adjustment and so forth. Further, each of these components is normally extremely stable over time when disposed in a stable environment. In addition, the position and orientation of each component can be carefully selected and accurately adjusted during assembly and/or alignment of the system, if need be. As a result, the physical configuration of each component and the overall effect it produces in that optical system can be accurately controlled and adjusted to meet the system's overall specifications. Thus, the overall optical system may be accurately characterized as the sum of its parts. Further, in most such systems, both the input and the output ends are accessible with the result that accurate measurement of the complete system is possible.

In contrast with such man-made optical systems, human and animal eyes are optical systems in which the individual internal components of a given eye are not normally separately accessible for either direct measurement or adjustment, the output of the optical system is not directly accessible for analysis and the characteristics of individual components change over time with growth, aging and other factors.

The most common reason for measuring the optical characteristics of a human eye is to determine a prescription for corrective lenses to correct vision problems. Such measurements of the optical characteristics of the eye have long been made by the actual or apparent substitution of lenses with various correction factors with the patient indicating the effect of each substitution in terms of the image being clearer or fuzzier. This technique determines an overall correction for the optical characteristics of the eye.

Such determinations are subject to experimental errors and such events as accommodation of the eye to the substituted lens in a manner which gives the impression that a particular correction is desirable, when in fact that correction is not optimum.

Further, these measurement techniques determine corrections which improve overall vision, but are limited in normal practice to prism, cylindrical and spherical corrections which are low order corrections to the patient's actual, detailed vision errors which include higher order terms or characteristics which these measurement techniques cannot determine.

For the most part these prior art measurement systems are subjective and require the active participation of the patient for their success. In such cases the ophthalmologist must rely on the patient to indicate accurately which images are clearer than others as an indication of the appropriate degree of correction. This requirement for active participation of the patient is a disadvantage in a number of circumstances such as in the diagnosis of small children who have difficulty in understanding what is being asked of them and prevents its use for infants who are incapable of indicating the effect of such lens substitutions.

The requirement for the active participation of the patient in the determination of the characteristics of the eye can have unfortunate effects. Some anomalous conditions result in permanent disabilities because they are not detected during infancy because of the inability of infants to communicate with ophthalmologists. For example, if one eye is in focus and the other is severely out of focus during the time the brain is developing its ability to interpret visual signals, then a permanent disability develops in which the out-of-focus eye is never able to contribute usefully to the brain's image recognition because of a lack of proper stimulation during the period in which the brain's image interpretation functions became established. A person suffering from this condition can tell with the affected eye whether the lines in an image are sharp or fuzzy, but cannot assimilate the perceived information into an image. Present subjective refraction measurement systems are incapable of determining the development of this condition in infants because they cannot accurately diagnose the visual acuity of the eye without the active participation of the patient.

A number of objective refractometers have been developed in the hope of overcoming these problems. However, each of these has had problems or deficiencies of its own. One common deficiency is accommodation by the eye being measured. Another common problem is determining and maintaining accurate alignment of the measurement system during the measurement cycle, since any misalignment can cause inaccurate results.

In recent years, substantial interest has developed in using laser sculpturing, i.e. ultraviolet (UV) light laser ablation, to shape the anterior surface of the cornea as a means of providing corrected vision in place of the use of glasses or contact lenses. U.S. Pat. No. 4,665,913, which is incorporated herein by reference, discloses a UV laser scanning ablation technique for shaping a cornea in which a laser beam which produces a small spot is scanned across the cornea to remove a desired thickness of corneal material on each scan. The area scanned is increased or decreased on subsequent passes to scan each portion of the corneal surface a number of times which is proportional to the thickness of material to be removed at that portion of the cornea.

An alternative to the direct shaping of the corneal surface, is to essentially permanently attach a lenticule to the cornea with the lenticule being shaped to provide the desired vision correction. We say "essentially permanent" because the intention is to leave the lenticule in place permanently, unless some problem should develop which requires its removal. Such lenticules themselves may be reshaped or reprofiled by laser ablation at the time of installation or subsequent thereto to compensate for changes in the overall characteristics of the eye. Such techniques are disclosed in more detail in U.S. Pat. No. 4,923,467, entitled, "Apparatus and Process for Application and Adjustable Reprofiling of Synthetic Lenticules for Vision Correction" by Keith P. Thompson, which is incorporated herein by reference.

In addition to the advantages provided by eliminating the need for eye glasses or contact lenses, both of these techniques are conceptually capable of providing substantial additional advantages in that each should, under proper control and with sufficiently detailed correction instructions, be able to produce fully asymmetric reshaping of the cornea in a practical manner, rather than being limited to the sphere, cylinder and wedge approximation mentioned previously.

However, in order to provide such detailed correction, there is a need for measurement techniques which measure the shape of the cornea and the existing refraction characteristics of the eye with the same detail and precision as can be provided by the correction modality in order that the errors may be fully corrected in this manner.

U.S. Pat. No. 4,669,466, which is incorporated herein by reference, discloses a system for providing an ophthalmic surgeon with data on the shape and thickness of the cornea to aid in making surgical decisions. That system measures the contour of the anterior surface of the cornea and the thickness of the cornea in order to provide the surgeon with data as to the present configuration and thickness of the cornea. That system is neither intended for nor capable of determining the refractive correction required for that eye. Rather, the surgeon must rely on a separately determined desired correction.

A measurement system providing such a correction measurement should be fast and should measure the eye's detailed refraction characteristics referenced to the cornea as a function of position across the dilated pupil. This position-dependent measurement may be categorized as a spatially resolved refraction measurement because the refraction at each measurement region (point) is determined in that local measurement region independent of the refraction at other, non-overlapping measurement regions.

Ideally, such a spatially resolved measurement system should be operable in both an objective mode which does not require the patient to interpret the quality of images and a subjective mode in which the patient determines the quality of the image. In that way, the best features of both techniques may be employed and the refraction of both cooperative and non-cooperative patients may be measured. As a desirable alternative, separate objective and subjective embodiments may be provided.

OBJECTS OF THE INVENTION

Accordingly, a primary object of the present invention is to provide an optical measurement system suitable for measuring the refractive characteristics of an eye in a spatially resolved manner.

Another object of the present invention is to provide an optical measurement system which relies on patient responses in measuring the refractive characteristics of the eye in a spatially resolved manner with the measurements referenced to the cornea.

Another object of the present invention is to provide an optical measurement system which relies on patient responses in measuring the refractive characteristics of the eye in a manner which minimizes adverse effects which result from accommodation.

Another object of the present invention is to provide an optical measurement system which does not rely on patient responses in measuring the refractive characteristics of the eye in a spatially resolved manner with the measurements referenced to the cornea.

Another object of the present invention is to provide an automatic optical measurement system capable of fully measuring an optical system in a spatially resolved manner in only seconds, and preferably in well under one second where the optical system is an eye.

Still another object of the present invention is to provide an automatic optical measurement system which avoids fatigue, eye motion and accommodation and which permits multiple measurements to be made.

A further object of the present invention is to provide an optical measurement system which provides the capability for automatic alignment.

A still further object of the present invention is to derive spatially resolved correction data from the spatially resolved refraction data.

A still further object of the present invention is to provide spatially resolved correction of vision.

SUMMARY OF THE INVENTION

The above and other objects which will become apparent from the specification as a whole, including the drawings, are accomplished in accordance with the present invention by determining the refractive characteristics of the eye in a spatially resolved manner. In accordance with this invention, these spatially resolved refraction measurements may made by both subjective and objective refractometers.

In accordance with a subjective refractometer embodiment of the present invention, a reference image or pattern and a measurement beam of light which is essentially collimated, are projected into the eye. The reference pattern and the measurement beam are preferably directed into the eye along two initially different optical paths which are merged into a single optical path by an appropriate optical mechanism such as a beam splitter. The patient controls manipulation of the measurement beam to properly position its image with respect to the reference image or pattern. This is preferably done directly by manipulation of a joystick or another input mechanism, but may also be done by verbal instructions to the ophthalmologist. For each measurement point on the cornea, the measurement beam is preferably held stationary at that measurement point while its impingement orientation relative to the optical axis of the refractometer is manipulated until the patient is satisfied that the image of the measurement beam is disposed in the desired relationship to the reference pattern.

During measurements, the eye must be properly aligned with respect to the refractometer. A desirable alignment choice is with the visual axis of the eye aligned with the optical axis of the refraction instrument. For this purpose we define the visual axis as the path of an optical ray that passes through the centroid of the pupil and strikes the fovea centralis. This visual axis may not be a straight line within the eye because this optical ray can bend through refraction at each of the optical surfaces within the eye. The fovea centralis, as is well known in the ophthalmic art, is that portion of the retina where the clearest image is produced and can be visually located as a substantially featureless depression in the retinal surface.

In this subjective embodiment, after correct alignment is obtained, the collimated measurement light beam projected by the refractometer is directed at a selected measurement point on the cornea. Typically, the beam diameter is chosen to be 1/5 to 1/10 of the diameter of the dilated pupil, such that measurements may be taken at between 25 and 100 separate measurement regions or "measurement points" on the cornea. At each measurement region, the beam direction is varied in response to patient inputs without changing the location at which the beam impinges on the cornea, until the patient sees the measurement beam as being properly aligned with respect to the reference pattern. The beam's angles, with respect to the instrument's optical axis in two perpendicular planes which include the instrument's optical axis describe the deviation of the beam direction from the optical axis. These angles are recorded and constitute the refraction information for that region of the cornea. The beam is then directed to another measurement point and the process of the patient aligning the measurement beam with respect to the reference pattern is repeated until measurements have been obtained at a desired set of measurement points.

A complete refraction measurement produces a record of these angle pairs for each measurement point. This record constitutes a refraction map of the eye which specifies the eye's refraction as a function of position on the cornea. For example, for an ideal or perfect eye which is perfectly aligned to the refractometer, the result for each measurement point would be 0° for each angle or an angle pair of 0,0. I.e., at each measurement point, the beam would strike the fovea centralis when it was parallel to the optical axis of the refractometer. For a real eye, most of the angles are likely to assume differing non-zero values. A conventional correction prescription in terms of prismatic, cylindrical and spherical corrections can be calculated rapidly from this information within a computer. However, considerably more information is contained within the refraction map. Thus, for example, the conventional refractive corrections can be subtracted within the computer from a full correction to indicate how well or poorly the conventional means can correct the eye. Alternatively, the full correction can be used in controlling a refractive correction technique such as a laser ablation to modify the refraction of the eye in a fully asymmetrical manner to produce a better correction than can be produced by conventional means.

In accordance with the invention, these measurements are preferably made by separately varying the location of the measurement point on the cornea and the direction of the beam at that measurement point.

In accordance with one embodiment, the actual or apparent position of the measurement beam light source controls the measurement beam impingement orientation, that is, the direction at which the measurement beam strikes the cornea relative to the optical axis of the refractometer (or the beams angles with respect to the optical axis in two preferably perpendicular planes, each of which includes the optical axis). A system for shifting the position of the light source serves as an impingement orientation imposer, i.e. controls the direction of the measurement beam with respect to the cornea. The beam is then passed through an aperture which narrows the beam and serves as a position shifter, i.e. selects the location on the cornea of the measurement point. That narrow beam is passed through a collimating lens which focuses the position shifting aperture onto the cornea. The aperture and the cornea are placed at conjugate locations with respect to the collimating lens so that the position of the scanning aperture determines the point on the cornea at which the measurement beam impinges independent of the beam orientation established by the orientation imposer. A beam splitter which combines the measurement beam and the reference pattern is preferably disposed between the collimating lens and the cornea. The reference pattern is separately provided, focused by a reference lens and reflected off the beam splitter toward the eye.

In accordance with an objective refractometer embodiment of the invention for use in measuring the eye, a measurement beam of light which is essentially collimated is projected through a measurement point on the cornea onto the retina where it forms a small illuminated spot. The retina of the eye is imaged onto a photosensitive detector which can determine when this small illuminated spot is essentially precisely centered on a target region on the retina. In response to the output of that photosensitive detector, appropriate electronics guide the movement of that illuminated spot to that target retinal region by generating electronic signals which result in the impingement orientation of the projected beam changing to one at which the illuminated spot is centered on the target region. One example of such a detector is a quadrant photodiode on which the retina is centered with its target region imaged on the origin of the quadrant photodiode. Preferably the origin of the quadrant photodiode is shifted into alignment with the image of the illuminated spot on the retina while the measurement beam of light is aimed along the optical axis of the refraction instrument and the visual axis of the eye.

During operation of this objective refractometer, the eye must be aligned and maintained in alignment for the short time (typically 10-30 milliseconds) required to take a complete set of refraction measurements. A desirable alignment choice is with the visual axis of the eye aligned with the optical axis of the refraction instrument. The eye can be aligned subjectively by the patient fixating on a target placed on the optical axis of the refractometer. Alternatively, correct alignment can be sensed objectively, as, for example, by viewing the position at which an undeflected projected beam from the refractometer passing through the pupil's centroid strikes the retina and moving the eye or the refractometer axis until this position coincides with the fovea centralis.

After correct alignment is obtained, the collimated light beam projected by the refractometer is scanned across the cornea. At each measurement region or point, the beam direction is varied without changing the point at which the beam impinges on the cornea until the position sensing detector determines that the beam is striking the fovea centralis. The beam's angles, with respect to the instrument's optical axis in two perpendicular planes constitute the refraction information for that region of the cornea. Using high speed circuit components, approximately 30 to 50 microseconds is required to complete the beam direction variation at each corneal measurement region. In this case, a complete refraction covering 100 distinct corneal regions can be completed in 3 to 5 milliseconds.

As an alternative to this measurement scheme, the beam direction may be set at a particular orientation and the beam scanned to the various measurement points and those measurement points for which the position sensing detector determines that the beam is striking the fovea centralis may be recorded as having that beam direction as their "optimum" orientation. The beam direction is then changed and the process repeated.

Since the refraction can be accomplished so quickly, the complete refraction can be repeated many times within a few seconds and the results compared to evaluate measurement quality.

In accordance with one embodiment, the measurement beam first passes through an orientation imposer which is a two dimensional beam scanner which provides an orientation-selected collimated beam. That beam is then passed through the position shifter which is a scanning aperture to provide a narrow beam. That narrow beam is passed through a collimating lens which focuses the scanning aperture onto the cornea. The scanning aperture and the cornea are placed at conjugate locations with respect to the collimating lens so that the position of the scanning aperture determines the point of impingement on the cornea independent of the beam orientation established by the orientation imposer.

In accordance with another embodiment, the orientation imposer is a first two dimensional beam deflector, the position shifter is a second two dimensional beam deflector effectively positioned at the focal point of the collimating lens. The orientation imposer and the tangent plane to the surface of the cornea are positioned at conjugate locations to the collimating lens, such as at twice the focal length (f) of the collimating lens with the cornea on the side of the collimating lens opposite the orientation imposer and the position shifter. The direction of deflection imposed by the first beam deflector controls the direction relative to the instrument's optical axis at which the measurement beam strikes the cornea. The second beam deflector determines the position (in two dimensions) at which the measurement beam strikes the cornea by displacing the measurement beam at the collimating lens a distance equal to $f\tan v$ from the reference position, where $v$ is the angle of deflection imposed on the beam by the position beam deflector as measured in the plane defined by the optical axis and the beam itself.

In either fully automatic embodiment, an image of the retina is separately formed on a photodetector for the purpose of determining the point on the retina at which the measurement beam strikes the retina. This retina imaging system may preferably comprise (1) a beam splitter (preferably polarizing) through which the measurement beam passes, preferably after passing through the collimating lens, (2) an additional polarizing filter (optional) and (3) a lens which focuses an image of the retina on the photodetector. The polarizing beam splitter and the polarizer in the retina imaging system serve to filter out light from a cross-polarized measurement beam which reflects off the surface of the cornea or the eye's lines. This minimizes the adverse impact of those corneal reflections (which may be brighter than the image of the retina) on the determination of the location of the bright spot on the retina.

The output from the photodetector is used to determine the location of the image of the beam on the retina. The measurement electronics adjust the beam orientation to move the image of the beam to a reference point such as the fovea centralis, without changing the measurement point. The photodetector may preferably be a quadrant detector or other sensor which provides an output which can be used to rapidly adjust the beam orientation to move the beam image to the reference point. Under these conditions, the system operates as a negative feedback loop to maintain the beam image in the null position (at the reference point) as the location of the measurement point is scanned across the eye. When implemented with suitable optics and high speed electronics, this overall system can obtain the data necessary for a hundred point map of the refractive characteristics of the eye in well under one second.

The spatially resolved refraction data, in combination with a measured existing surface contour of the anterior surface of the eye, enable the calculation of a detailed (spatially resolved) new contour for the anterior surface of the eye which will provide corrected vision. This new contour is provided by detailed (spatially resolved) modification of the contour of the anterior surface of the eye, as by laser ablation.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawings in which:

FIGS. 9-11 are illustrations of an alternative embodiment of the projection portion of the FIG. 4 system; and FIGS. 12A and 12B are diagrams of geometric relationships at a measurement point.

DETAILED DESCRIPTION

In order to determine the refractive characteristics of an eye, in accordance with the present invention, a narrow, collimated measurement light beam is directed to selected measurement points on the cornea of the eye, one measurement point at a time. While holding the measurement beam to impinging on the cornea at the selected measurement point, the direction or orientation of the measurement beam relative to the refractometer system's axis (that is, the measurement beam's impingement orientation or direction) is adjusted until the measurement beam strikes the retina in a location associated with desired or optimum performance in accordance with the criterion being employed for the refraction measurement. Once that direction or orientation has been determined for a given measurement point, a different measurement point is selected and the process is repeated.

Figure 1:
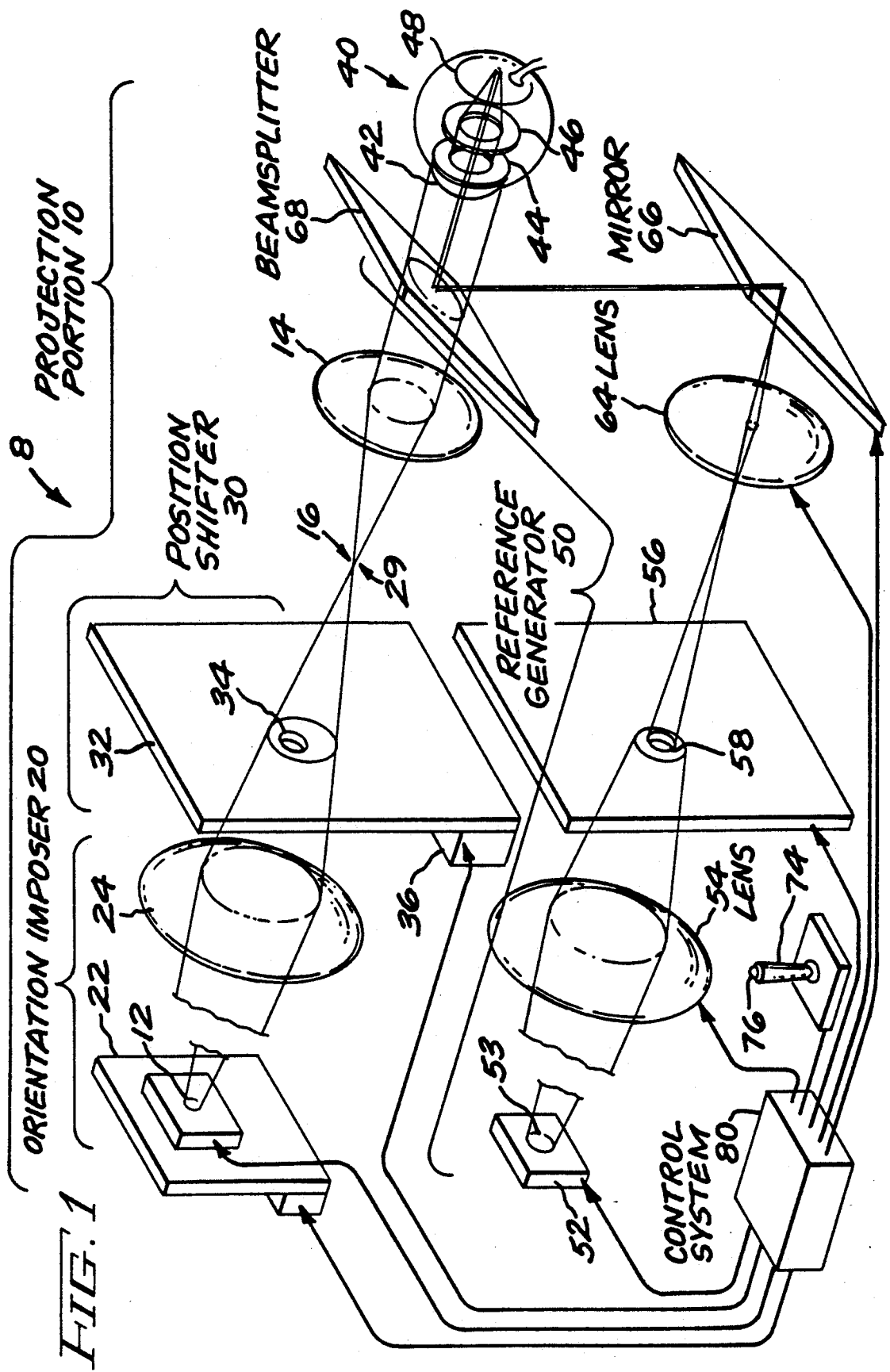
FIG. 1 is a perspective, schematic illustration of one embodiment of a subjective refractometer in accordance with the present invention.

Since vision involves both physical optics within the eye and physiological effects within the image processing portions of the mind, we consider it preferable to involve a cooperative patient in the determination of when the beam is in the position which corresponds to optimum image formation. To this end, in a first, subjective refractometer embodiment of the present invention, we include a reference image generating portion 50 for providing a reference image with respect to which the patient adjusts the measurement beam into a desired optimum relationship. In the refractometer embodiment 8 illustrated in a perspective view in FIG. 1 and as an optical diagram in FIG. 2, a reference image generation system 50 comprises a source 52 of a reference image 53, a shaping lens 54, an opaque member 56 having a beam size restricting aperture 58 therein, a reference collimating lens 64, a mirror 66 and a beam splitter 68. The opaque member 56 serves to prevent the light which forms the reference pattern from flooding the cornea and the aperture 58 therein allows the light which forms the reference pattern to enter the eye in the vicinity of the center of the pupil. This is to minimize distortion of the reference pattern as a result of any existing refractive errors. To this end, the opaque member 56 is positioned where reference collimating lens 64 conjugates it to the cornea 42. The lenses 54 and 64 focus the reference image 53 onto the retina of the eye and are positioned with a common focal plane disposed between them with their axial focal points which are disposed in that focal plane co-incident and respectively conjugate with respect to the image source 52 and the retina 48 whereby the image source 52 is positioned conjugate to the retina 48. The mirror 66 bends the reference optical path toward the optical axis of the eye and the beam splitter 68 bends the reference optical path into the eye substantially concentric to the eye's optical axis while allowing the measurement beam which is separately provided by a projection portion 10 of the refractometer to pass directly through the beam splitter to reach the eye substantially parallel to the eye's optical axis. Thus, beam splitter 68 preferably merges the reference image and the measurement beam to cause them to appear to the eye as two parts of a single image. In FIG. 1 the distance between the lens 64 and the eye 40 is excessive compared to the distance between the lens 14 (to be discussed subsequently) and the eye. These two distances are preferably the same in the actual system. In the drawing the need to fit all of the elements of the Figure on the drawing sheet results in the lens-64-to-eye distance being exaggerated.

Figure 3A:
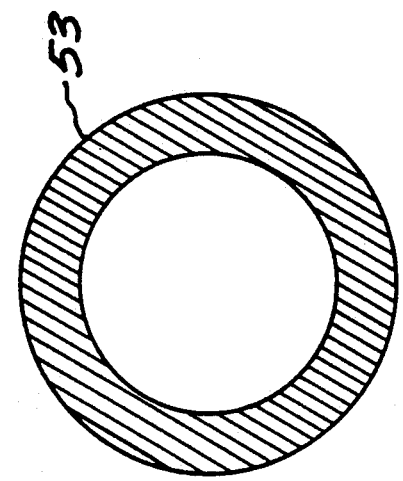
FIGS. 3A, 3B and 3C illustrate images observed by the patient during the use of the FIG. 1 refractometer.

A vast number of reference images may be used in accordance with the particular vision characteristics of the patient and the portion of the eye to be measured. For reasons to be discussed subsequently, our preferred reference image comprises an illuminated circular annulus 53 as illustrated in FIG. 3A. It may be considered desirable to provide a discrete fixation target such as a cross within the reference image 53 in order to aid the patient in maintaining eye fixation throughout the measurement process. However, that is generally unnecessary in this embodiment since the reference pattern itself serves as a fixation target. The pattern shown in FIG. 3A is the image the patient sees (1) with a reference image which does not include a separate fixation target while (2) the measurement beam 18 (to be discussed subsequently) is turned off or blocked. We prefer to have the patient adjust the focus of the annulus 53 at the beginning of the measurement process so that it appears sharply defined to the patient. This adjustment of the focus of the annulus 53 is to minimize the effect of any existing refractive errors on the measurements to be taken.

This adjustment to sharp focus may be done manually by the patient adjusting the position of the collimating lens 64 or the position of the reference image source 52 with respect to the position of the collimating lens 64. Alternatively, it may be done under electronic control by the patient manipulating a joy stick 74 which is connected to a control system 80 which then, in turn, controls the position of either the collimating lens 64 or the reference image source 52, and/or other components of the reference portion of the system. As a further alternative, the adjustment may be done by the ophthalmologist in response to responses from the patient.

The eye is generally properly aligned with respect to the optical axis of the refractometer when the patient is "looking at" the reference pattern.

With these preliminary adjustments completed, the system is ready to perform a refraction on the patient's eye.

A projection portion 10 of the refractometer 8 comprises a point light source 12 which may preferably be a light emitting diode (either an incoherent diode or a laser diode, as may be preferred).

For this subjective refractometry system, the light source 12 provides a beam of visible light which the patient can see in order to make the decisions and/or adjustments required in the process of performing the refraction measurements.

Figure 2:
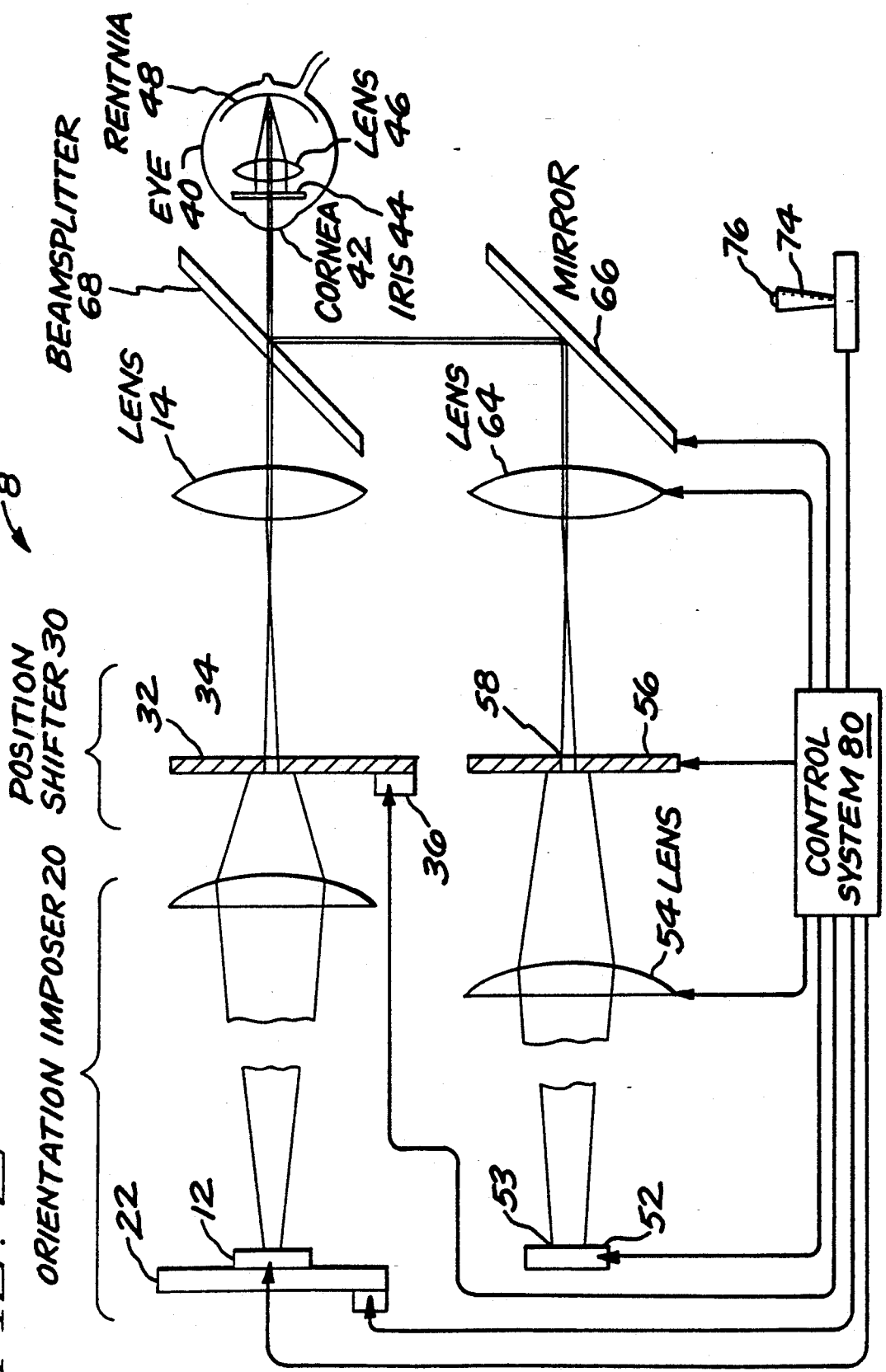
FIG. 2 is an optical diagram of the subjective refractometer of FIG. 1.

The position of the light source 12 is controlled by an impingement orientation imposer 20 which operates under the control of the control system 80. A light source 12 should be disposed at a distance from orientation imposer 20 which renders its light rays substantially parallel at the angle imposer. The light source 12 may be mounted on an X-Y table or stage 22 or any other mechanism which is suitable for shifting the position of the light source in the X-Y plane in the FIG. 1 and 2 illustrations. The X-Y stage 22 should be capable of providing accurate, repeatable small changes in the position of the light source 12 in a manner in which the control system 80 is accurately informed of the actual position of that light source. The light emerging from the light source 12 passes through a lens system 24 which focuses that light into a beam which is focused in the focal plane of the lens system 24. This focus of the beam to a point in the focal plane is provided independent of the setting of the X-Y stage. As an alternative to movement of the light source itself, the position of the light source may be fixed with the light from the light source being reflected by a galvanometer mounted mirror whose orientation is controlled by control system 80 to provide an effect like that produced by moving the light source in the plane in which the X-Y stage is disposed in FIG. 1.

After passing through the lens system 24, the light from light source 12 passes through a position shifter 30 whose function is to control the location of the measurement point on the cornea. In the illustrated embodiment, the position shifter 30 comprises an opaque member 32 whose position in the X-Y plane is controlled by control system 80 via a position drive system 36 which may be another X-Y stage. The opaque member 32 has a single, small aperture 34 therein. In FIG. 1, the full pattern of the measurement light beam is illustrated as though member 32 were transparent. FIG. 2 illustrates a beam pattern present in the system during actual use, i.e. with the member 32 being treated as being opaque except for its aperture 34. As will be observed, only a portion of the light from light source 12 passes through the aperture 34 to comprise the beam 18 (FIG. 2) with the remainder of the light being blocked by the member 32. In a manner to be discussed subsequently, the position of the aperture 34 controls the location of the measurement point on the cornea. The size of the aperture 34 also controls the size of the portion of the cornea which constitutes a measurement point, that is, the size of the portion of the cornea whose refractive characteristics affect the data at that measurement point. The measurement beam at the cornea is preferably small in diameter compared to the area of the dilated pupil (also referred to as the active portion of the cornea) and preferably has a diameter of about 0.5 to 1 mm or less (about 1/10 to 1/5 of the diameter of the dilated pupil). The dilation of the pupil may be as a result of dark adaptation or medication or other causes. Dilation of the pupil is not essential, but in absence of dilation, measurements are limited to that portion of the corneal surface through which light of the measurement beam can reach the active retina. Such restricted data limits the quality of the correction which can be provided.

After passing through the aperture 34, the light passes through the focal plane of the lens system 24 at a point whose location is determined by the position of the aperture 34. Thereafter, the light beam expands until it reaches the collimating lens 14. The collimating lens 14 is positioned with its focal plane coincident with the focal plane of lens system 24 and with its focal point 16 coincident with the focal point 29 of the lens system 24. Upon emerging from the collimating lens 14, the light beam is collimated with parallel rays because the incident light beam was focused in the focal plane of the collimating lens 14. This narrow beam 18 of parallel light rays (FIG. 2) then passes through the beam splitter 68. The beam splitter 68 is not a necessary part of the projection portion 10 of the refractometer, but is present to combine the measurement beam 18 and the reference image 53 into a single image as seen by the eye. The measurement beam enters the eye via the cornea 42 at the selected measurement point and is refracted by the cornea which provides much of the eye's refraction. Thereafter, the measurement light beam is further refracted by the lens 46 of the eye and finally strikes the retina 48 of the eye.

The position shifter 30 and the measurement surface (cornea 42) of the eye 40 are positioned with respect to the collimating lens 14 so that they are at conjugate surfaces. In general, conjugate surfaces, are paired surfaces associated with a lens. A characteristic of conjugate surfaces for a lens is that any light passing through a given point in the first conjugate surface (on the first side of the lens) will pass through the corresponding or conjugate point in the second conjugate surface (on the second side of the lens). This is true independent of the light's orientation at the first conjugate surface, so long as that light passes through the lens rather than passing beyond its outer edge. Specifically, if the member 32 and the cornea of the eye are disposed on opposite sides of a collimating lens and each is positioned twice the collimating lens' focal length from the collimating lens, then the member 32 and a tangent plane to the cornea (perpendicular to the axis of the projection system) are conjugate surfaces. Consequently, any light passing through an aperture 34 in the member 32 will also pass through the corresponding measurement point on the cornea of the eye. It is in this manner that the position of the aperture 34 determines the location of the measurement point.

The direction of propagation of (also referred to as the orientation of) the measurement beam where it strikes the cornea is determined by the direction or orientation of the measurement beam at the focal plane of the collimating lens. For a properly configured refractometer, if the orientation imposer 20 is set so that the rays emerging from the lens system 24 are focused above the axial focal point 16 of collimating lens 14 (that is, angled upward), then the light rays emerging from collimating lens 14 are disposed parallel to each other, but angled downward at a corresponding angle. If the orientation imposer 20 is not imposing a deflection on the light beam, the light rays emerging from the lens system 24 are focused at the axial focal point of collimating lens 14 (that is, the light rays are parallel to the optical axis), then those light rays are disposed parallel to the axis of the optical system when they emerge from collimating lens 14. If the orientation imposer is set so that the light rays emerging from the lens system 24 are focused below the axial focal point 16 of collimating lens 14 (that is, angled downward), then those light rays emerge from collimating lens 14 angled upwards relative to the axis of the optical system. As a result, for these three conditions, the light rays at the corresponding measurement point on the cornea are traveling, respectively, downward, parallel to and upward with respect to the optical axis. It will be understood that this type of relationship applies also to beams which are angled relative to the YZ plane, the YZ plane being the plane of the paper in the drawing. In all cases, the beams will impinge on the cornea at the same point because the collimating lens 14 conjugates points on member 32 at the cornea, i.e. it focuses an image of the member 32 onto the cornea. This ability of the imposer to control the orientation at which the light ray impinges on the cornea surface without changing the position where it meets the cornea is important in this technique for measuring the refraction of the eye as is described hereinafter. The impingement orientation or direction is set relative to the optical axis of this refraction instrument (i.e., it is *not* the angle of incidence of the beam on the cornea, that is, it is *not* measured relative to the normal to the cornea surface at the measurement point).

It will be recognized that if the aperture 34 in the member 32 were large enough, the entire active portion of the cornea would be illuminated by the measurement beam. The small size of the aperture 34 serves to block any portion of the light beam emerging from the lens system 24 which would strike the cornea outside the desired measurement point and has no effect on the orientation of the measurement beam at the cornea for a properly focused beam emerging from the lens system 24.

At a measurement point where the eye exhibits refractive error, a narrow beam of light oriented parallel to the optical axis of the refractometer does not get refracted to the fovea centralis, but rather is refracted to some other location. However, there is another orientation for a narrow light beam at that measurement point which results in the beam being refracted to the fovea centralis. The difference in orientation of these two beams is a measure of the present refractive error at that measurement point. It will be recognized, that the orientation of that off-orientation beam is defined by its angle with respect to the optical axis of the refractometer system in the Y-Z plane and its angle with respect to that optical axis in the X-Z plane.

Figure 3B:
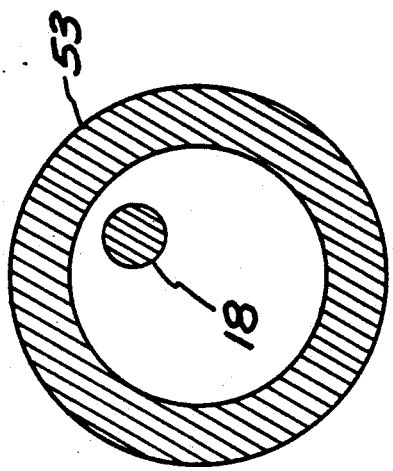
Figure 3C:
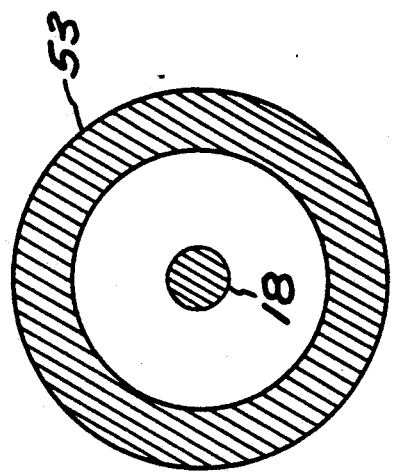

For a measurement beam which is oriented parallel to the optical axis of the refraction system at a measurement point where the eye exhibits refractive error, the image seen by the patient will appear in some fashion like that illustrated in FIG. 3B in that the image of the measurement beam 18 will not be centered in the center of the blank (nonilluminated) disk in the middle of the annulus 53. With the joystick now connected to control the position of the light source 12 by controlling the X-Y stage 22 (or mirror, if used), the patient manipulates joystick 74 to bring the image of the measurement beam 18 into the center of the annulus 53, as illustrated in FIG. 3C. As is known from target rifle shooting, the human eye and mind together can determine when a small disk is centered within the open center of an annulus with great accuracy. It is for this reason that the annulus 53 is a preferred reference pattern for this subjective refraction measurement. When the patient concludes that the image 18 is centered in the annulus 53, the patient presses the joystick button 76. At that point, the control system records or stores the position of the X-Y stage 22 as the measured data for that measurement point. The recorded information may be the physical positioning of the X-Y stage (or mirror or other orientation control structure) or the beam angles in the X-Z and Y-Z planes which result from that position or any other appropriate data. Recording that data completes the process of measuring the refraction of the eye at that measurement point. The control system 80 may be considered as a means for storing data representative of the position and/or orientation of the measurement pattern when said measurement pattern is in the desired relationship centered within the annulus 53. The control system 80 may also be considered as a means for providing data indicative of the refraction of the eye. The control system 80 then causes the position shifting drive system 36 to shift the member 32 to place the aperture 34 in a new location which corresponds to the next desired measurement point. Once again, the patient manipulates the joystick to center the image 18 in the annulus 53 and presses the joystick button when it is centered.

Use of this reference pattern measurement beam positioning technique minimizes the problem of accommodation because the bulk of the image perceived by the patient remains fixed throughout the measurement process because no lenses are substituted in front of it and only the initial position of the measurement beam changes from measurement point to measurement point.

This process is repeated at each desired measurement point on the cornea until all of the desired measurement data has been taken. This measurement process can include repeating measurements at each measurement point more than once in order to ascertain that the data is accurate, or at least repeatable. Further, substantially identically data for the same measurement point taken at different times provides assurance that the eye was still in the same location and orientation at the time of the repeated measurements as it was at the time of the original measurement. Several substantially identical measurements at each measurement point ensure that the eye has remained stationary during the measurement process and that the data is therefore valid.

One advantage with this subjective system is that the process of making the measurement can help in obtaining and retaining a child's attention by presenting it as being like a video game in which the goal is to center the measurement beam spot in the central disk of the reference pattern.

For use with a non-cooperative patient, an objective, automatic refractometer is preferred. Such an objective, automatic refractometer system 108 in accordance with the present invention is illustrated in a perspective, stylized view in FIG. 4 and in a side view as an optical diagram in FIGS. 5 and 6. Automatic refractometer system 108 comprises a projection portion 110, a sensing portion 150 and a control system 180. In both FIGS. 4 and 5, the full pattern of the light beam is illustrated as though the scanning disk 132 within the projection portion 110 were transparent. FIG. 6 illustrates a beam pattern present in the system during actual use, i.e. with the scanning disk 132 opaque except for its scanning apertures.

The autorefractometer 108 comprises a light source 112 which provides a narrow collimated beam of light having a frequency to which the components of the eye in front of the retina are transparent and to which the retina is at least partially reflective or scattering. Thus, this light source may preferably be a laser which emits visible, UV or infrared radiation. In this specific embodiment, the laser beam is preferably vertically polarized. The beam from this laser passes through beam impingement orientation imposer 120 which may be an acoustic/optical (A/O) scanner 122 in combination with a lens system 124. In accordance with control signals applied thereto, the scanner 122 is capable of deflecting the angle of the beam in both the vertical and horizontal directions simultaneously. Other two dimensional beam deflectors such as galvanometer mounted mirrors may also be used.

The light beam emerging from (A/O) scanner 122 passes through the lens system 124 which is shown in this schematic illustration as being a telescope including lenses 126 and 128. This beam of light, when it emerges from the lens 128, is converging toward a point in the focal plane of the lens system 124, independent of the selected measurement beam orientation.

A position shifter 130 comprised of a scanning disk 132 is positioned in the path of the light beam emerging from the orientation imposer for the purpose of establishing the position of the measurement point on the cornea. This is done by restricting the light beam to a small cross-section (narrow beam) (FIG. 6) which is appropriate for making the desired measurements of the refraction of the eye. The location of the aperture which narrows the beam controls the location in which this narrow light beam strikes the cornea. This narrowed laser beam is preferably small in diameter compared to the area of the optically active portion of the cornea and preferably has a diameter of about 0.5 to 1 mm or less.

This scanning mechanism (rotating disk 132) scans the measurement beam or measurement point along the surface of the eye in a predetermined pattern. However, we use "scan" as a general term which is free of implications as to the particular type of scan pattern employed. Depending on the scanning mechanism employed, the measurement point may be scanned in a continuous manner or in steps or jumps separated by pauses between such movements along the surface of the eye. Such pauses may be uniform or of varying length. The scan pattern may follow a predetermined path (such as a raster scan), may follow a random path or a path which is dependent on the results of previous measurements, or any other desired path.

After passing through the scanning disk 132, the light comes to a point in the focal plane of lens system 124, after which the light beam expands until it reaches a collimating lens 114 having its focal plane coincident with the focal plane of lens system 124 and its focal point 116 coincident with the focal point 129 of lens system 124. Upon emerging from the collimating lens 114, the light beam is collimated with parallel rays because the incident light beam was focused in the focal plane of the collimating lens 114.

This narrow beam of parallel light rays then passes through a beam splitter 168 which preferably passes vertically polarized light and reflects horizontally polarized light. Substantially all the light in the beam passes through the beam splitter, because none of the operations performed on the beam has the effect of changing its polarization. Beam splitter 168 is part of the sensing portion 150 of the system rather than the projection portion 110. The light beam is refracted by the cornea 142 of the eye 140, is further refracted by the eye's lens 146 and finally strikes the eye's retina 148.

The scanning disk 132 and the measurement surface (cornea 142) of the eye 140 are positioned with respect to the collimating lens 114 so that they are at conjugate surfaces.

Figure 4:
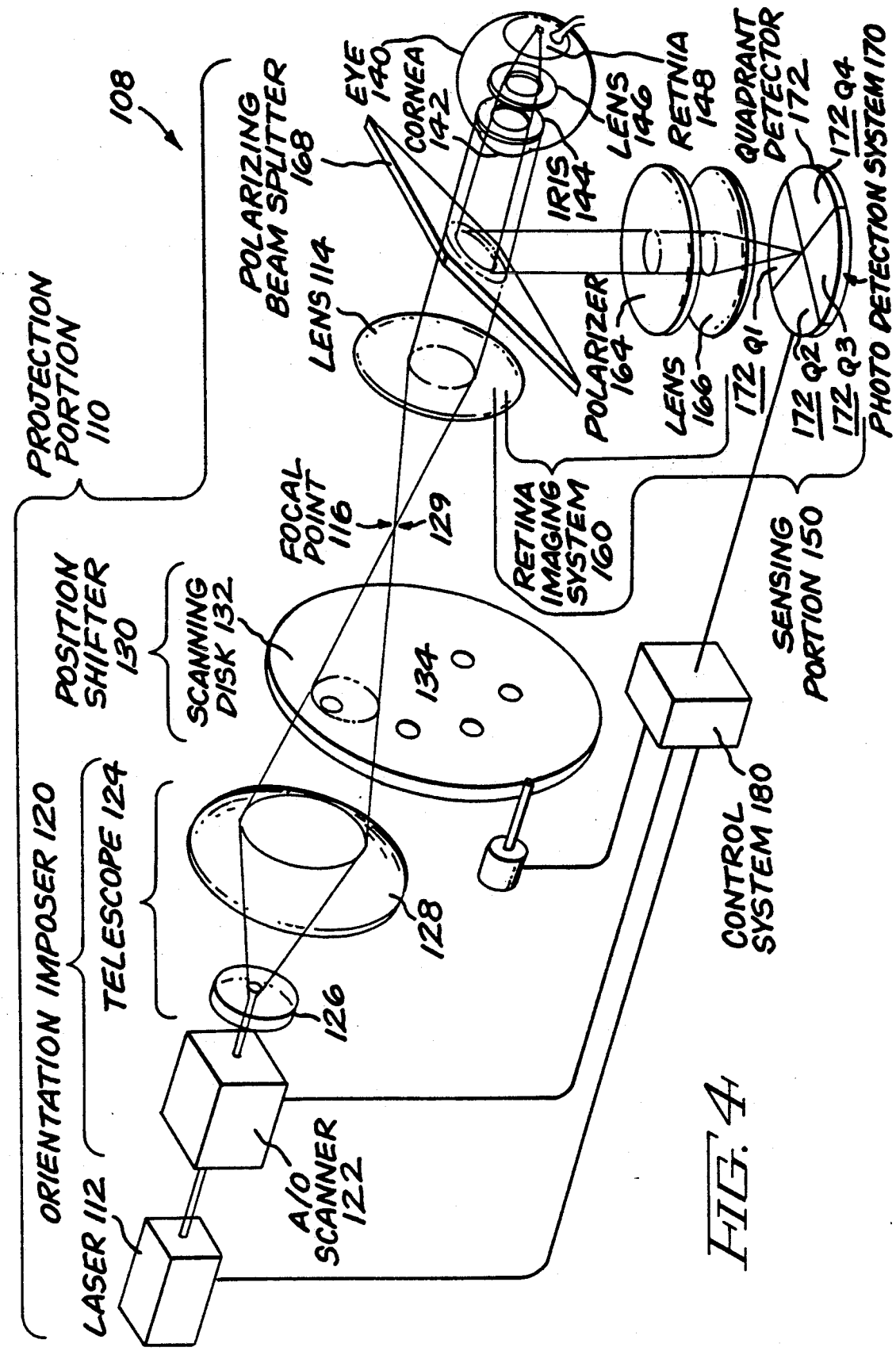
FIG. 4 is a perspective illustration of an autorefractometer in accordance with the present invention.
Figure 5:
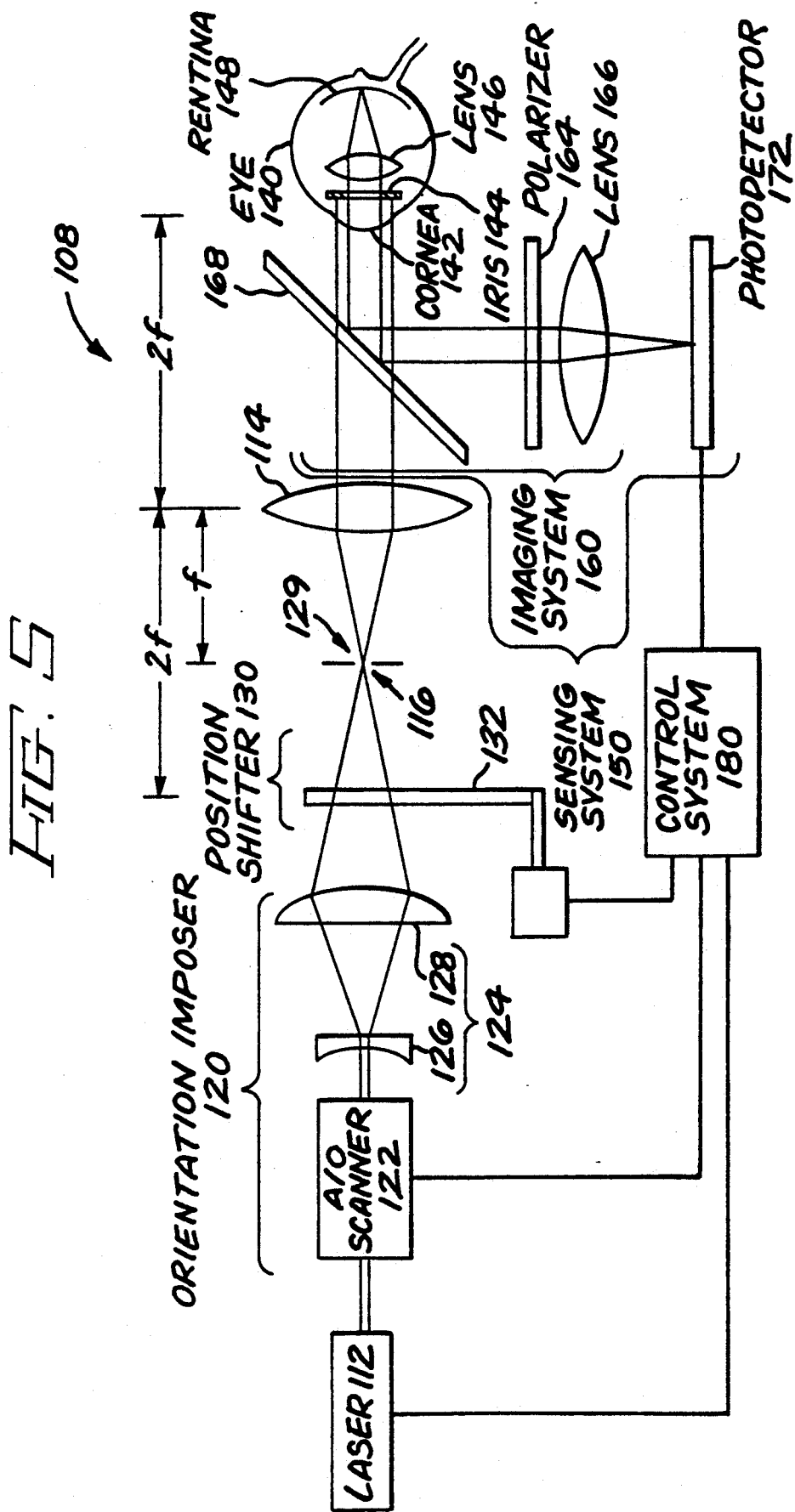
FIGS. 5 and 6 comprise optical diagrams of the structure of FIG. 4 under different conditions.
Figure 6:
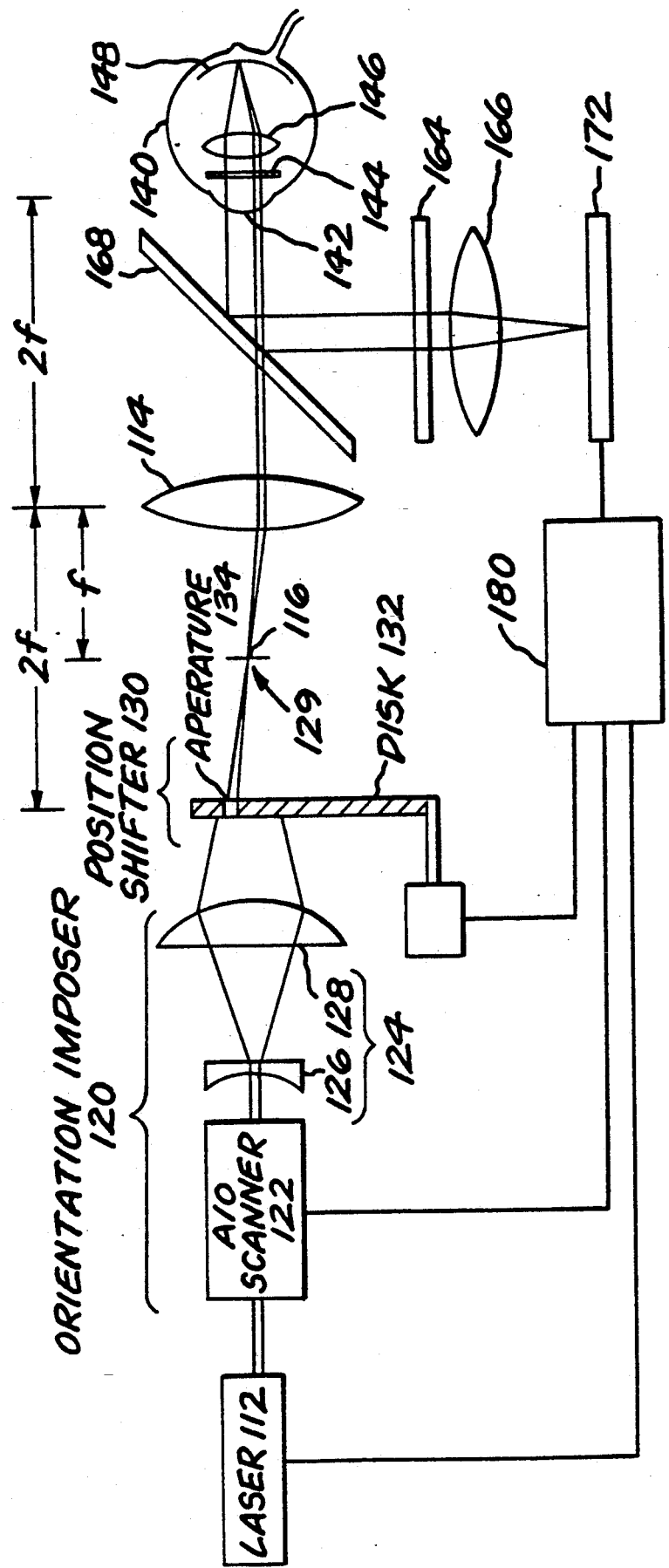

The light beam in FIGS. 4 and 5 subtends, encompasses or spans the entire active part of the cornea at all useful beam impingement orientations in order to ensure than any desired beam impingement orientation (relative to the optical axis) can be provided at any given measurement point.

What is actually present at the measurement surface or cornea is an image of the scanning disk 132. However, since only the scanning aperture 134 (about 0.5-1 mm in diameter) in the scanning disk transmits light, the rest of the scanning disk's image is dark and we observe the 0.5-1 mm diameter light beam from hole 134 as though it were the entire image.

Together, the position shifter 130 (scanning disk 132) and the orientation imposer 120 (scanner 122 and lens system 124), under the control of the control system 180 independently control both the position at which the beam strikes the cornea and the impingement orientation at which it strikes the cornea. This capability is of general utility and not restricted to this particular application.

The measurement region of the cornea at which the measurement beam is directed may be at any desired location on the cornea. For perfect refraction, a measurement beam which is disposed parallel to the visual axis should impinge on the retina at the fovea centralis. If the measurement beam strikes the eye in the center of the fovea centralis, then the eye's refraction at this measurement point is considered optimum.

A fraction of the light which strikes the retina is scattered by the retina. This scattered light leaves the retina in all directions. The portion of this scattered light which strikes the eye's lens 146 is refracted, continues on toward the iris 144 (which blocks any portion outside the pupil), continues on to the cornea 142 where further refraction takes place as the light emerges from the cornea into the ambient atmosphere. On emerging from the cornea, the rays of light will be parallel for an eye having optimum refraction. This emergent beam of light then enters the sensing system 150 by striking the surface of the beam splitter 168 which reflects the horizontally polarized portion of that light toward a photodetector 172. The beam splitter 168 is preferably chosen to pass one state of polarized light and to reflect the other polarization state. The polarization of the projected laser light is chosen to be in the "pass" state (vertical in this example) so that substantially all of that projected light beam will pass through the beam splitter and strike the cornea. Light reflected off the cornea and the eye's lens back toward the beam splitter will primarily pass through the beam splitter and only be reflected weakly by the beam splitter because reflections off a smooth surface at relatively small angles with respect to the surface normal are by nature so-called Fresnel reflections in which the reflected light is strongly polarized in the same direction as the incident light. However, the light scattered off the cells of the retina is partially-to-completely depolarized and thus will be significantly reflected by the beam splitter. In this way, a clean image of the measurement beam spot on the retina can be obtained without clutter from the reflections off the cornea and lens of the eye. Any remnants of clutter from the Fresnel reflections can be further filtered by a polarization filter 164. The remaining light is then focused on the photodetector 172 as an image of the retina by a retina imaging lens 166.

This interaction of the measurement beam with the eye is shown schematically in the optical diagram in FIG. 6. The incident beam is narrow and collimated because of the nature of its production. In contrast, the light pattern emerging from the eye is substantially wider than the incident beam because of the scattering at the retinal surface which produces that beam.

The position photodetector 172 is preferably composed of four separate quadrants $172_{Q1}$-$172_{Q4}$. Such a quadrant detector provides an output signal indicating which quadrant or quadrants of the detector have the most light impinging on it or them and, therefore, in which quadrants of the detector the image of the illuminated spot on the retina is predominantly located. The control system 180 processes the output signals from the quadrant detector 172 and generates control signals for the orientation imposer 120 which set an orientation which brings the beam spot on the retina to a reference point on the retina. The origin of the quadrant detector is placed so that the image of the retina reference point is centered there. This reference point is the point at which it is desired to have parallel-to-the-axis rays focus. The reference point is normally the fovea centralis.

A reference point other than the fovea centralis may be selected. However, it is preferred in most cases to select the fovea centralis as the reference point, since that ensures that the refractive correction determined will in fact result in focusing an image disposed on the optical axis at infinite distance at the point of maximum visual acuity. During measurements on a cooperative patient, this reference point is preferably established at the fovea centralis by asking the patient to fixate on the measurement light beam when it is on axis and its set impingement orientation is zero. The quadrant detector is then shifted so that the image of the beam spot on the retina is centered at its origin so that its output indicates that the beam is centered at the reference point.

Figure 7:
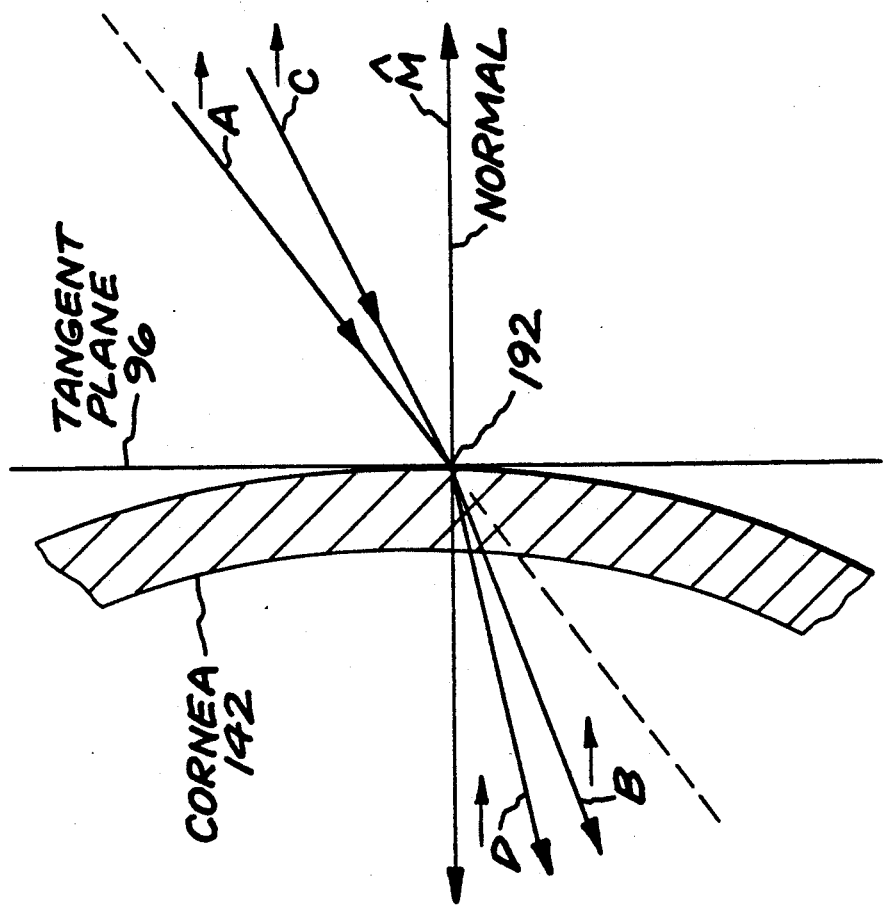
FIG. 7 illustrates conditions at a measurement point.

FIG. 7 is a diagram illustrating an incident ray $\bar{A}$ disposed parallel to the optic axis which is refracted by the cornea at a measurement point 192 into the beam $\bar{B}$ which strikes the retina below the fovea centralis and an incident ray of light $\bar{C}$ disposed at an angle to the optic axis which is refracted by the cornea at measurement point 192 into the beam $\vec{D}$ which strikes the retina at the fovea centralis. $\hat{M}$ is the normal to the tangent plane 96 at the measurement point 192. How small a cross-section the measurement beam needs to have depends in part on the desired measurement accuracy, in part on the focusing limits of light and in part on how rapidly the refractive characteristics of the eye change with position. The size of the measurement region is determined by the size of the measurement beam. For a small enough measurement beam, the measurement region may be called a measurement point. The term "measurement point" is also used as the point at which the center of the measurement beam is directed, independent of its size. For refractions which vary slowly with the position, a larger beam cross-section can provide more accurate data because the diffractive nature of light allows a larger beam to be focused into a tighter spot on the retina. Thus, reducing the measurement beam's cross-section only improves measurement accuracy up to a point. As illustrated in FIG. 7, the angle of the ray of light $\vec{C}$ is substantially displaced from the optical axis for drawing clarity. It is this deflection (in two dimensions) of the incident beam from parallel to optical axis which provides the data which enables the refraction of the eye to be determined.

Where the visual axis is treated as the Z-axis of an XYZ coordinate system, the XY plane can be located tangent to the cornea at its intersection with the visual axis. The orientation of the measurement beam may be uniquely specified by specifying its angle in the XZ plane relative to the normal $\hat{M}$ and in the YZ plane relative to the normal $\hat{M}$.

Conceptually, a parallel-to-the-axis measurement beam is directed at each measurement point on the cornea and the general direction of the resulting bright spot's displacement from the fovea centralis is determined from the output of the quadrant detector. In response to that output signal, the control system 180 sets the orientation imposer 120's A/O scanner 122 to deflect the orientation of the beam to cause the bright spot to move closer to the fovea centralis. When that bright spot is centered in the fovea centralis, it is centered in the quadrant detector whose output signal then indicates that all the quadrants are receiving substantially equal illumination at which point the deflection angles (vertical = YZ-plane and horizontal = XZ-plane) imposed by the A/O scanner 122 are recorded along with the location of the measurement point on the cornea as a data point for a corneal map of the eye's refractive characteristics.

Where a quadrant detector is used to detect the location of the bright spot on the retina, the parallel-to-the-axis beam produces no quantitative data, unless the bright spot for such a beam is centered in the fovea centralis. Consequently, in the interest of system simplicity, speed and elegance, an initial beam or ray oriented parallel to the refractometer's optical axis is used only with the first data point of a scan (as a default position). Thereafter, the measurement beam deflection angle is maintained at its deflected value as the measurement point is scanned across the eye and the quadrant detector's output is used as a feedback signal to adjust the A/O scanner angle to maintain the bright spot centered in the quadrant detector as the measurement point (beam) moves. Thus, this system operates on the null principle in which feedback control signals are used to maintain the bright spot centered in the quadrant detector with the control signals themselves providing the measurement data, rather than in an open loop manner in which the position of the bright spot must be continually measured, with the measured position of the bright spot being the data. Since measuring the position of the bright spot is a time consuming process, the null system of this invention can operate much more rapidly than an open loop system. Further, it provides substantially increased measurement accuracy over that provided by an open loop system. Consequently, this system can accurately measure the refractive characteristics of the eye in almost unbelievably short times.

Figure 8:
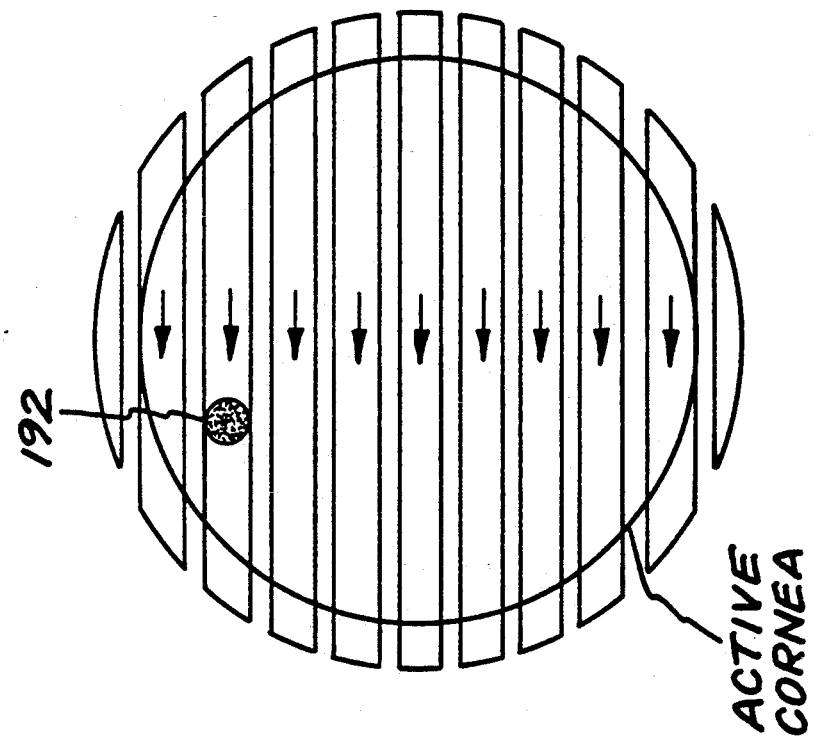
FIG. 8 is an illustration of a measurement beam scanning pattern produced by the system of FIG. 7.

The scanning pattern across the eye with use of the scanning disk 132 is illustrated in FIG. 8. In this pattern, each scan line is scanned in the same direction as successive apertures in the disk come into alignment with the laser beam. Successive scans are all in the same direction and the size of a measurement point 192 is determined by the size of the apertures 134. Each aperture 134 in the scanning disk controls scanning across a strip of the cornea which, although actually an arc, is essentially straight because of the small portion of the scanning disk subtended by the light beam from the lens system 124. The individual scan lines are illustrated as being spaced apart vertically for drawing clarity. It will be understood that in an actual system, they may be spaced apart, just contiguous or overlapping, depending on the positioning of the apertures 134 in the scanning disk 132.

With a constantly rotating scanning disk 132, the locations of measurement points along the scan line for a given hole in the disk is determined by the point in time at which the data is taken. Acoustic/optic scanners, quadrant detectors and electronic systems, are available which are fast enough to institute a change in the impingement orientation of the measurement beam and determine the effect of that change in less than 10 microseconds in this null system. This makes it possible to take measurements at a rate of one every 30 microseconds if no more than three orientation adjustments are needed per measurement point on the average. One measurement point every 30 microseconds corresponds to 100 measurement points in 0.003 second. Once a given aperture 134 in the scanning disk has scanned past the active area of a cornea, the next lower aperture in the scanning disk comes into the beam from the telescope and starts the next higher scan across the cornea. With the scanning disk rotating at 18,000 rpm, a complete revolution of the scanning disk takes 0.0033 second. Consequently, the entire scanning of the eye can be done in 0.0033 second. This total scanning time is fast enough that the eye does not accommodate (that is, refocus) in response to the stimulation provided by the measurement light beam. At a nominal disk speed of 1,800 rpm the entire scan pattern would be completed in 0.033 second. Preferably, a map having from about 25 to 100 data points is generated in order to provide detailed information on the existing refractive characteristics of the eye. More or fewer data points may be used as may be preferred. A scanning disk 132 may be used in the FIG. 1 system 8 for measurement point control, provided that the light source 12 is pulse or flashed in synchronism with the rotation of the scanning disk so that the light source is only on when the aperture 134 is positioned at the measurement point at which data is presently being taken.

For scan line sweeps of the type illustrated in FIG. 8, the orientation which results in the bright spot being centered in the fovea centralis is expected to vary relatively smoothly with position along the scan line for typical corneal configurations. Abrupt changes are expected only with a relatively rough surfaced (injured or diseased) corneas. Thus, the setting of the A/O scanner 122 deflection angle will normally vary in a smooth manner which requires only minor variations in the deflection setting to keep the bright spot centered in the fovea centralis as the measurement point moves across to the eye.

A major advantage of this null scanning technique is that the control system 180 operates essentially as a negative feedback loop which continuously adjusts the A/O scanner 122 to keep the bright spot centered in the quadrant detector (at a null). The use of the scanning disk which scans across one "strip" of the cornea at a time provides the ability to take data points as close together along that strip as may be considered desirable. It is only at the transition between different apertures in the scanning disk (which control the scanning across different strips of the cornea), where a significant abrupt change in orientation required from the orientation imposer 120 should occur. However, the orientation imposer setting for the beginning of one scan line can be expected to be similar to the orientation for the beginning of the previous scan line. Consequently, if desired, during the "dead" time between scan lines, the scanner can be switched from its end-of-the-first-scan-line value back to its beginning-of-the-first-scan-line value in anticipation of the beginning of the second scan line in order to minimize feedback loop settling time.

At the beginning of each scan line in FIG. 8, the measurement beam is preferably positioned on the cornea in a location where it strikes the iris rather than passing through the pupil. The iris scatters this incident light in a manner quite similar to that in which the retina scatters the incident light. Consequently, even with the use of a polarized system, substantial light will reach the quadrant detector while the beam is impinging on the iris. The intensity of the light striking the quadrant detector will be substantially greater while the beam is striking the iris than it is when the beam is striking the retina. This is (1) because of the small portion of light which is scattered by the retina rather than being absorbed and (2) because of the relatively small solid angle of the light scattered by the retina which can reach the quadrant detector as compared to the solid angle for which light scattered by the iris can reach the photodetector.

While this relatively high intensity light striking the quadrant detector when the beam is on the iris might initially seem to be a problem, it is actually a benefit in that it enables automatic alignment of the system and automatic tracking of the alignment of the system. In particular, the topmost aperture in the scanning disk should result in the beam striking the iris for the full scan. The first aperture for which the measurement beam passes through the pupil will have a brief period of low intensity light impinging on the photodetector 172. During that time, useful data will be taken. As successive apertures scan the eye, the period of low intensity light on the quadrant detector will increase until the scan which crosses the center of the eye. Thereafter, the period of low intensity light on the quadrant detector will decrease with successive scans until there is no period of low intensity. For proper alignment, the "circle" of beam position for which low intensity illumination strikes the quadrant detector should be centered in the scan pattern. We say "circle" because although the pupil is often thought of as being circular, many pupils are not perfect circles. Consequently, proper alignment of the system can be checked after the data is taken. Further, while the data is being taken, any unexpected substantial offset in the point at which the low intensity portion of the scan begins or ends is an indication that the eye has moved relative to the measurement system. Thus, proper alignment is automatically determined and checked.

Proper alignment can be checked in the initial stages of the scanning process if, instead of the aperture pattern illustrated in FIG. 4 in which successive apertures are disposed on a single inwardly curving spiral, the apertures are alternated between the outermost aperture and the innermost aperture working successively toward the middle aperture. In that way, the first aperture scans the bottom of the cornea, the second aperture scans the top of the cornea, the third aperture scans the next strip toward the center of the eye at the bottom of the cornea, the fourth aperture scans the next strip toward the center of the eye at the top of the eye and so forth. In this manner, for a properly aligned system with a circular pupil, the system is properly aligned when after the first scan in which the beam passes through the pupil, every following scan of the beam passes through the pupil. If that does not occur, then the eye is misaligned with respect to the measurement system and realignment is desirable prior to taking the measurements.

During the time the quadrant detector output is large because the measurement beam is striking the iris, the beam impingement orientation does not need to be adjusted, since the beam cannot strike the fovea centralis and thus its image cannot be centered in the quadrant detector. Pinning of the orientation adjustment portion of the electronics at a maximum deflection angle in an attempt to center this "image" is preferably avoided by including a threshold detector in the orientation adjustment portion of the control system to freeze the orientation for quadrant detector outputs in excess of the threshold value.

Control system 180 serves many functions in this system. It provides appropriate control signals to the orientation imposer and the position shifter, it receives the signals from the position sensor, establishes the locations of the measurement points, determines the impingement orientation for each measurement point, stores the measurement values for subsequent use or output and so forth. This storage is preferably in electronic form, but may also be provided in paper or other forms. The control system can also perform the data reduction which is discussed hereinafter in connection with determining appropriate corrections for the measured eye and so forth.

One disadvantage of the system 108 of FIG. 4 is the fact that it is rather inefficient in the use of laser power. In particular, the laser beam which emerges from the hole in the scanning disk is a small fraction of the overall area of the beam striking the disk. The resulting waste of laser power is of concern from an efficiency point of view. Also of possible concern is the fact that if the scanning disk were, for some reason, removed from the apparatus and the apparatus were turned on with a patient's eye in the measurement position, the full laser power would be incident on the eye. That could cause damage to the eye.

Figure 9:
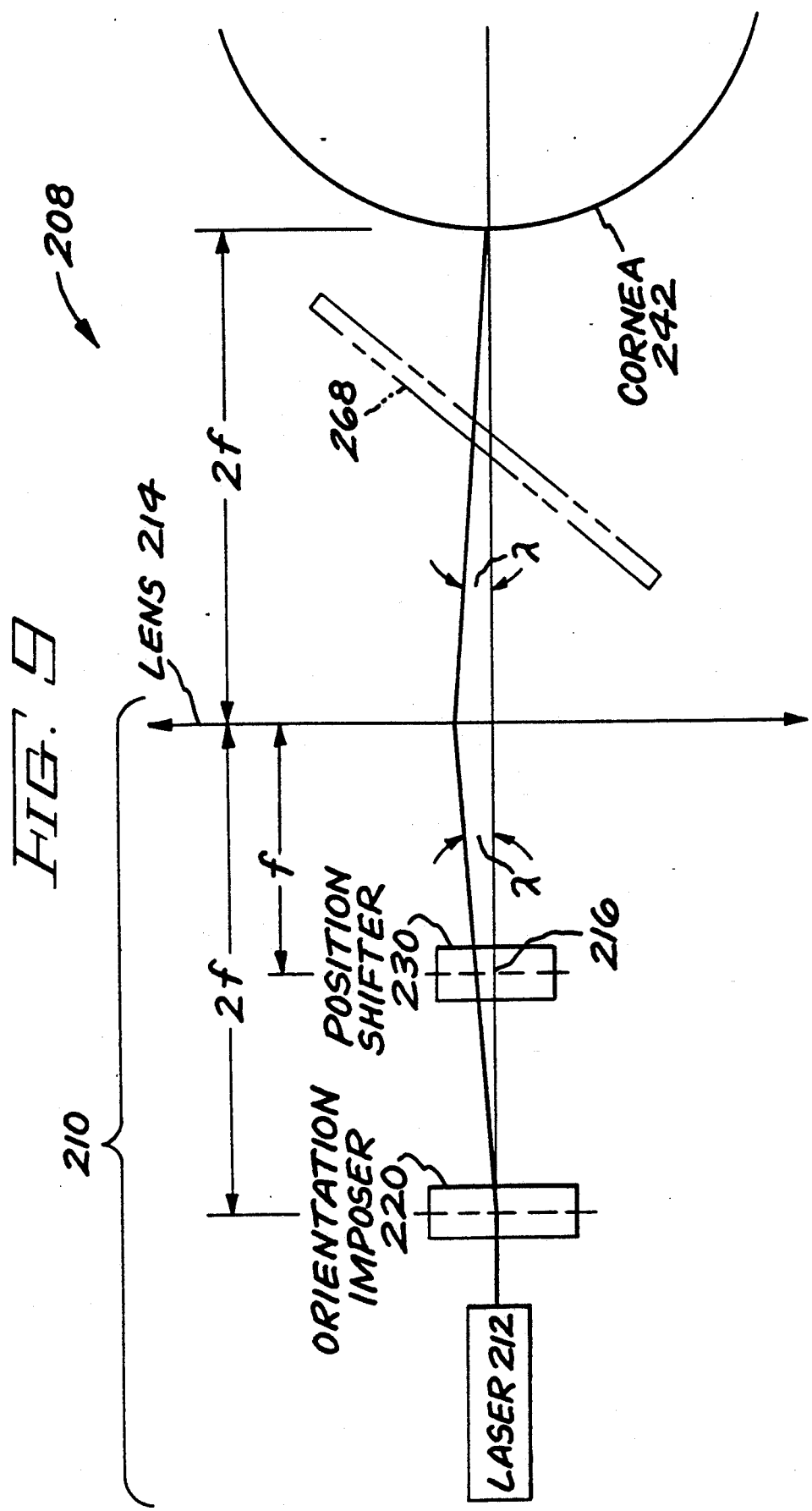
Figure 10:
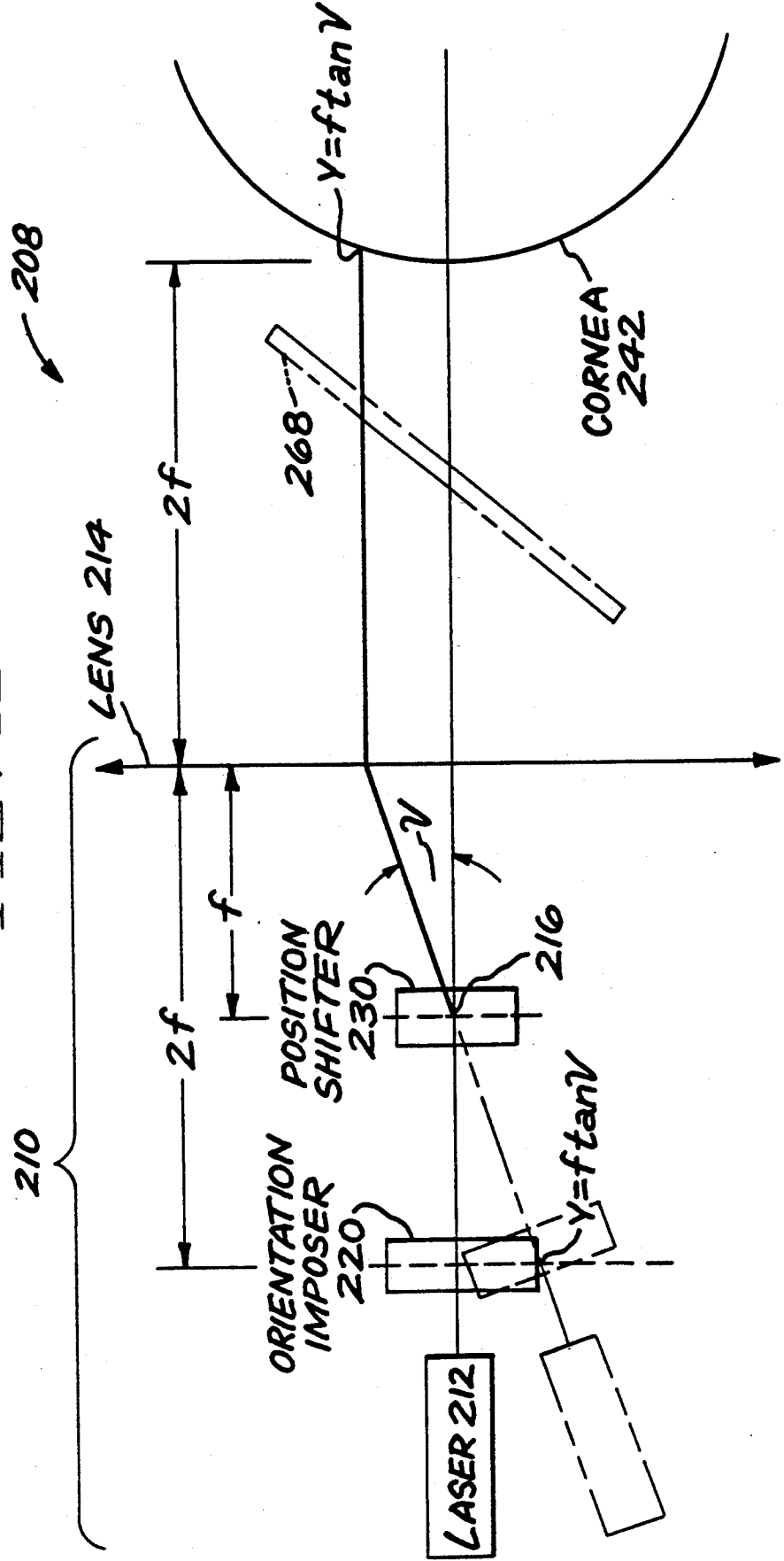

These potential disadvantages of the FIGS. 4–6 embodiment of the invention are avoided in accordance with an alternative embodiment 208 illustrated in FIGS. 9–11. In the system 208, reference numerals which are higher by 100 than corresponding reference numerals in the system 108 identify portions of the system which perform substantially the same function as their corresponding system 108 components. In system 208, the sensing portion of the system, the control system and the internal components of the eye are omitted for drawing clarity. It will be understood that in FIGS. 9–11, they would be similar to those shown in FIGS. 4–6. In FIG. 9, the cornea 242 of the eye is positioned at twice the focal length f of the collimating lens 214 from the collimating lens. The beam splitter 268 serves the same purpose as the beam splitter 168 in system 108. To the left of the collimating lens 214, an orientation imposer 220 is positioned at twice the focal length of the collimating lens from the collimating lens and thus is conjugate to the cornea. Also on the left-hand side of the collimating lens is a position shifter 230 which is positioned at the focal plane of the collimating lens and preferably centered at the focal point of the collimating lens. The laser 212 provides the measurement light beam.

Suitable devices for use as the orientation imposer 220 are acoustic/optic scanners, galvanometer mounted mirrors or other devices. Suitable devices for use as the position shifter 230 are galvanometer mounted mirrors or other devices. Acoustic/optic scanners are not suitable at this time because of their requirement that the incident beam be disposed strictly on and parallel to their axis. It will be recognized that where galvanometer mounted mirrors are used to control the deflections which select the orientation or position, the optical axis will not be a straight line, but will be reflected at each of the mirrors. However, the effect will be similar. The orientation imposer 220 and the measurement surface (cornea) may be positioned at any conjugate locations for which the distance from the collimating lens is greater than f, so long as the angled beam emerging from orientation imposer 220 passes through the two-dimensional position shifter 230 in its active region.

FIG. 9 illustrates the system with the orientation imposer 220 set to introduce a deflection angle while the position shifter 230 is set to an on-axis setting (no deflection). It will be noted that the light beam in the deflected position still strikes the cornea at the same point as it would without the orientation imposing deflection because of the conjugate locations of the orientation imposer 220 and the cornea 242.

In FIG. 10, the system is illustrated with the orientation imposer 220 set to a parallel-to-the-axis setting (no deflection) and the position shifter 230 set to position the beam at a desired, off-axis, measurement point on the cornea. It will be noted that the position at which the beam strikes the cornea is displaced from the optical axis by a distance in the Y-direction of $f\tan v$, where $v$ is the angle of deflection in the YZ plane introduced by the position shifter 230. This is simply the focal length f length of the collimating lens times the tangent of the angle of deflection set by the position shifter. This geometric formula is well known. This position offset is a result of the deflection introduced by the position shifter 230 placing its emergent beam at an orientation which causes that ray to be coincident with the direction of an undeflected ray from a point in the left-hand 2f plane which is that distance ($f\tan v$) below the optical axis (a point which the collimating lens conjugates to the corresponding conjugate point at the opposite 2f plane (i.e. at the cornea)). This is true for all angles $v$ which do not deflect the beam outside the collimating lens. While in FIG. 10 the illustration is for the YZ plane, it will be understood that for a position which is not in the YZ plane, this same diagram applies for that position's component in the YZ plane since that component is established by the Y deflection imposed by the position shifter 230. In that situation, there would a be a similar diagram which would apply in the XZ plane for the component of the beam's position in the XZ plane which is controlled by the X-direction deflection established by the position shifter 230.

In FIG. 11, the system 208 is illustrated with both the orientation imposer 220 and the position shifter 230 set to provide deflections. In particular, the orientation imposer 220 is set to produce the same deflection as in FIG. 9 and the position shifter 230 is set to provide the same deflection as in FIG. 10. It will be noted that the position at which the measurement beam strikes the cornea is unchanged by the addition of the orientation deflection and the orientation at which the measurement beam strikes the cornea relative to the optical axis of the projection portion 210 of the system (the beam's relative orientation) is unaffected by the position displacement. Consequently, the position of the measurement point and the orientation of the incident beam are independently controlled.

System 208 has the advantage that the entire laser beam is used in the measurement process. Consequently, system 208 is much more efficient in its use of laser energy than system 108 is and reduces or eliminates the risk of exposure of the eye to an unintended high intensity of light. Further unlike the system 108 which uses a scanning disk, the position setting for the system 208 may be randomly controlled in any desired manner since the position is controlled by the position shifter 230 which can be a random access device.

It will be noted that where a galvanometer mounted mirror is used to produce the deflections which establish the position of the beam, then the position deflection may be slightly displaced from the focal plane of the collimating lens for some angle deflection settings. Such variations can be compensated for by a correction table which once measured and determined, remains invariant for the corresponding orientation and position deflection settings. It will be further recognized that the significance of any offset from the focal plane depends in part on the focal length f of the collimating lens. Where the focal length of the collimating lens is relatively long, such deviations from the focal plane will have a smaller effect than where the focal length of the collimating lens is quite short. It will be recognized that other small aberrations may be present in either mirror or acoustic/optic scanner systems, but that in the detailed engineering design of such systems, those aberrations can be measured and compensated for if they have an undesired effect on the measurement accuracy.

While the system 208 is preferably operated in the same manner as has been described for the system 108, that is by selecting a measurement point and adjusting the impingement orientation of the measurement beam to cause that beam to be refracted to the fovea centralis, it is also conceivable (in either system) to instead set an impingement orientation and then map the locus of positions for which that deflection angle results in the beam being centered in the fovea centralis. However, such a procedure is not at this time preferred, unless it is being used to check measurements of refraction errors which have already been performed such that the expected locus of such points is already known and thus may be swept in an efficient manner. Alternatively, in a fixed orientation scan mode, the quadrant in which the bright spot is located can be determined and recorded for each measurement point as a means of expediting the process of finding the optimum orientation for each measurement point by selecting orientations for subsequent scans which should approach optimum for selected measurement points at which optimum values have not been determined.

While it is preferred to place the beam splitter between the collimating lens 114 or 214 and the eye, it should be recognized that the beam splitter can be placed in other locations (such as between the positioner and the collimating lens) as long as it still achieves its purpose of deflecting light emerging from the eye toward the position sensing photodetector.

Both subjective and objective embodiments of a refractometer in accordance with the present invention have been illustrated and described with corresponding orientation imposition and control systems and techniques. It will be recognized that these various techniques are not limited to use with the particular type of system (subjective or objective) in which they have been disclosed, but may be used in the other type as well.

While separate objective and subjective embodiments have been illustrated and described, both embodiments may be incorporated in the same refractometer by providing for substitution of a reference generator for a sensor system or vice versa. Alternative or combined projection portions may also be employed.

In order to determine how to correct the refractive errors determined during the measurement process, the existing contour of the cornea or lenticule is measured separately using an instrument such as the CMS Keratometer produced by Computed Anatomy, Inc. The angle of a normal to the corneal surface at each measurement point (perpendicular to a plane tangent to the cornea surface at that measurement point) or equivalent contour data is determined and stored in association with its measurement point. For each measurement point, the desired change in refraction obtained from the current invention and the orientation of the existing normal to the surface-to-be-shaped obtained from the keratometer may be used to determine the change in the surface configuration required to cause a light ray disposed parallel to the optical axis and striking the cornea at the measurement point to impinge on the retina in the fovea centralis.

The determination of the required surface angle change is made using Snell's law, the index of refraction ($n_1$) of the material on the side of the measurement surface away from the eye (typically 1.0003 for air) and the index of refraction ($n_2$) of the material on the side of the measurement surface toward the retina (typically 1.34 for the cornea) in combination with the measured beam impingement angle for a measurement light beam striking the fovea centralis and the angle of the normal to the existing surface at the measurement point. The relationships used in determining the angle of a normal to the surface of the cornea which provides proper refraction at a measurement point are illustrated in FIGS. 12A and 12B.

Figure 12B:
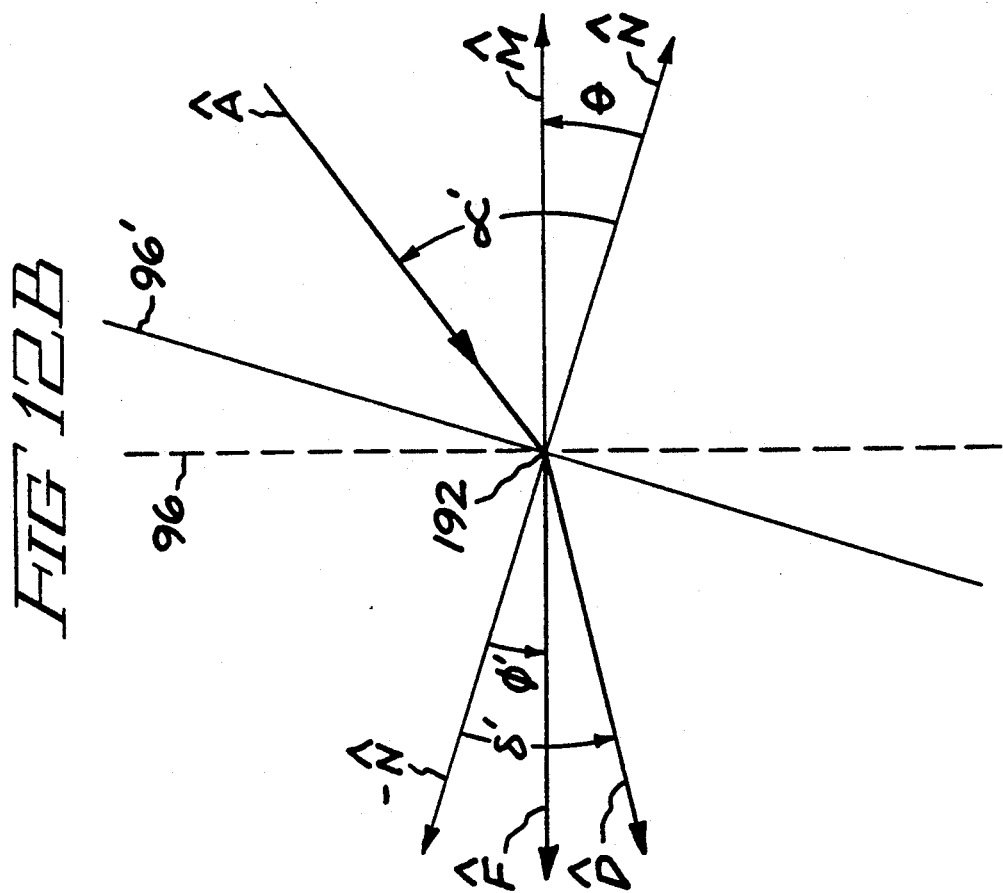

During the initial portions of the following discussion, the angles indicated in FIGS. 12A and 12B should be ignored. In FIGS. 12A and 12B, the surface of the cornea is omitted from the figure for drawing clarity. A plane 96 tangent to the corneal surface at a measurement point 192 has a normal $\hat{M}$. An initial trial beam arrives at the measurement point 192 along the unit vector $\hat{A}$. The unit vector $\hat{A}$ is parallel to the reference incident beam direction which will generally be parallel to the optical axis of the eye and the measurement system. In passing from the air into the cornea, the incident beam is refracted and continues on a path coincident with the unit vector $\hat{B}$, passes through the eye's lens and strikes the retina (neither shown) outside the fovea centralis. With a refractometer in accordance with this invention, an incident vector direction $\hat{C}$ is found which results in refraction of that beam along the vector $\hat{D}$ within the cornea which results in the beam striking the retina in the center of the fovea centralis. Thus, the measurement data recorded for this measurement point is the vector direction $\hat{C}$.

In order to provide corrected refraction, the angle of the corneal surface should be changed to have a tangent plane 96' in FIG. 12B. The new tangent plane 96' has a normal $\hat{N}$ which is displaced from the normal $\hat{M}$ to the existing tangent plane 96. The new tangent plane 96' must be chosen so that a beam incident at the measurement point along the unit vector $\hat{A}$ will be refracted by the cornea along the unit vector $\hat{D}$. For derivation of the relationship between the normals $\hat{N}$ and $\hat{M}$, an additional unit vector $\hat{F}$ is shown in FIG. 12B which represents the direction of refraction of the beam $\hat{A}$ for the general case of a changed normal. The normal $\hat{N}$ which produces proper refraction is found by setting the vector $\hat{F}$ equal to the vector $\hat{D}$.

During the analysis of the changes to be made in the corneal surface, the assumption will be made that the angle of the corneal surface is changed without changing its position. In actual practice, the position change is likely to be small enough that it can be ignored. However, those skilled in geometry will recognize that it is straightforward to include this surface position shift in the relationships developed here by adding a translation to the coordinate system transformation used hereinafter during this explanation. However, such translation is omitted here for simplicity and clarity of the discussion. For simplicity and clarity in the discussion, the relationship between the normals of the uncorrected and a corrected corneal surface will be calculated for the simplified case wherein the surface normals and all the vectors defined above lie in a single plane. This simple case is illustrated in FIGS. 12A and 12B when it is assumed that all vectors lie in the plane of the paper. It is also directly applicable to any cornea or portion of a cornea whose anterior surface is essentially cylindrically symmetric about the visual axis through the region of interest and the only refraction changes required preserve that symmetry. This is also a good approximation to the rigorous solution for cases involving moderately asymmetric corneas.

Those readers for whom the derivation of equation (21) below is not of interest can skip to the paragraph containing Equation (21).

Turning now to the derivation of the relationship between the normals in which all vectors and normals are in a single plane, the angle $\alpha$ is the angle of the unit vector $\hat{A}$ from the unit normal vector $\hat{M}$ and $\beta$ is the angle of the unit vector $\hat{B}$ from the unit normal vector $-\hat{M}$. In this explanation, counterclockwise rotation is taken as positive. Thus, in the illustration both $\alpha$ and $\beta$ are positive. The air in front of the eye has a refractive index $n_1$ and the cornea itself has a refractive index $n_2$. The relationship between the vectors $\hat{A}$ and $\hat{B}$ are given by Snell's Law as:

$$\sin \alpha = n \sin \beta \tag{1}$$

where $$n = n_2/n_1 \tag{2}$$

We can solve equation (1) for $\beta$ in terms of $\alpha$ which yields:

$$\beta = \arcsin[n^{-1}\sin \alpha] \tag{3}$$

During the process of measuring the refraction at measurement point 192, it is found that a beam in the direction of the unit vector $\hat{C}$ when incident at the point 192 is refracted to strike the retina in the fovea centralis. In passing into the cornea, the beam $\hat{C}$ is refracted into the beam $\hat{D}$. Beam $\hat{C}$ is at an angle $\chi$ to the normal $\hat{M}$ and is displaced from the beam $\hat{A}$ by a rotation through an angle $\epsilon$. The angle $\chi$ is related to the angles $\alpha$ and $\epsilon$ by the following equation:

$$\alpha + \epsilon = \chi \tag{4}$$

The diffracted beam $\hat{D}$ is disposed at an angle $\delta$ relative to the normal $-\hat{M}$. In a manner similar to Equation (3), the angle $\delta$ may be expressed as:

$$\delta = \arcsin[n^{-1}\sin(\alpha + \epsilon)] \tag{5}$$

Turning now to FIG. 12B, the angle of the initial trial beam $\hat{A}$ relative to the new surface normal $\hat{N}$ is $\alpha'$ where the new normal $\hat{N}$ is obtained from the old normal $\hat{M}$ by rotation through the angle $\theta$ as shown, $\alpha'$ may be expressed as follows:

$$\alpha' = \alpha - \theta \tag{6}$$

it being noted that $\theta$ is a rotation in the negative sense in this illustration. The light beam along the unit vector $\hat{A}$ is diffracted by its passage into the cornea along the unit vector $\hat{F}$ which is disposed at an angle $\phi'$ with respect to the new surface normal $-\hat{N}$. By equation (1):

$$\sin \alpha' = n \sin \phi' \tag{7}$$

substituting for $\alpha'$, yields:

$$\sin(\alpha - \theta) = n \sin(\phi') \tag{8}$$

which may be solved for $\phi'$ to obtain:

$$\phi' = \arcsin[n^{-1}\sin(\alpha - \theta)] \tag{9}$$

The angle between the desired diffracted beam direction $\hat{D}$ and the normal $-\hat{N}$ is $\delta'$ which may be expressed as:

$$\delta' = \delta - \theta \tag{10}$$

The surface normal $\hat{N}$ required to provide proper refraction for this region of the cornea is obtained when the unit vectors $\hat{D}$ and $\hat{F}$ are coincident. Thus, the desired new normal vector $\hat{N}$ is obtained by setting $\phi' = \delta'$ and solving the equations. More particularly, $$\phi' = \delta' = \delta - \theta \tag{11}$$

or $$\phi' = \delta - \theta \tag{12}$$

Substituting the value of $\phi'$ obtained in equation (9) and the value of $\delta$ obtained in equation (5) yields $$\arcsin[n^{-1}\sin(\alpha - \theta)] = \arcsin[n^{-1}\sin(\alpha + \epsilon)] - \theta \tag{13}$$

which simplifies successively to:

$$n^{-1}\sin(\alpha - \theta) = \sin\{\arcsin[n^{-1}\sin(\alpha + \epsilon)] - \theta\} \tag{14}$$

$$\sin(\alpha - \theta) = n\sin\{\arcsin[n^{-1}\sin(\alpha + \epsilon)] - \theta\} \tag{15}$$

For any given measurement point, the values of $\alpha$, $\epsilon$ and n will be known. Consequently, equation (15) can be easily solved for $\theta$ which is the desired change in surface angle by methods of graphing, computer analysis or approximation. In an actual measurement system, because of the number of data points in the measurement of a single eye, this analysis will be done by computer in a manner which is straightforward. This equation can be solved explicitly when the arguments of the sin functions are sufficiently small that the approximation:

$$\sin x = x \tag{16}$$

which also implies:

$$\arcsin x = x \tag{17}$$

is valid. It is normally considered that this approximation is valid for arguments of less than 6 degrees. Using equations (16) and (17) to simplify equation (15) leads successively to:

$$\alpha - \theta = n \arcsin[n^{-1}(\alpha + \epsilon)] - n\theta \tag{18}$$

$$(n-1)\theta = n[n^{-1}(\alpha + \epsilon)] - \alpha \tag{19}$$

$$\theta = \epsilon/(n-1) \tag{20}$$

The index of refraction for the cornea is approximately 1.33, thus, the denominator is equation (2) is equal to 0.33 and:

$$\theta = 3\epsilon \tag{21}$$

Thus, the deviation of the new $\hat{M}$ normal-to-the-surface from the old-normal-to-the surface $\hat{N}$ is three times the deviation between the vectors $\hat{A}$ and $\hat{C}$.

While the value $\theta = 3\epsilon$ is only valid for small angles, most refractive errors fall in this range. For those situations in which the refractive errors are larger, equation (15) may be easily solved by computer so long as all of the vectors are disposed in a common plane.

For those situations in which the simplifying assumption that all of the vectors are in a common plane does not hold, a derivation similar to that given above may be done for the general situation where the position of each vector must be specified by its components in two different planes. Where the Z axis of a rectangular coordinate system S is disposed coincident with the normal $\hat{M}$, the vectors are specified by their angles of deviation from the Z axis in the ZX and ZY planes. The new normal $\hat{N}$ is then coincident with the Z' axis of a transformed coordinate system S'. Such a transformation is straightforward for one of ordinary skill in the arts of geometry including transformations of coordinate systems.

While the method for determining the new desired normal $\hat{N}$ has been derived using simplifying assumptions in order to be tractable in this patent, it will be understood that in a refractometry system employing this invention, all of the data reduction is expected to be done by computer and presumably in software. As such, the required transformations and calculations can be done very rapidly with almost any desired degree of accuracy in order to produce a map of the cornea specifying the desired new normal at each of the measurement points. Alternatively, these calculations may be done once for common values and stored as a look-up table, with resort to detached calculation being reserved for anomalous cases whose values are not in the table.

For clarity and conciseness, the exposed surface of a lenticule which is attached to the eye or the cornea of an eye which has no lenticule attached thereto is referred to as the anterior surface of the eye. It will be understood that by anterior surface of the eye, we mean the exposed surface of the cornea or the lenticule. That anterior surface may or may not have the epithelium present thereover in accordance with the condition being discussed. During measurement of the refractive characteristics of the eye, it is preferred to have the epithelium and tear film present. During shaping of the anterior surface of the eye by laser ablation, it is customary to remove the epithelium before performing the shaping.

Once the desired new normal $\hat{N}$ to the surface has been determined for each measurement point, a new surface contour which will provide those desired normals $\hat{N}$ at each data point may be determined. This may preferably be done beginning at the optical axis of the eye and working outward from there to beyond the visually active portion of the lenticule or cornea.

In determining the new surface contour, experience with the effect of minor deviations from perfect refraction should be taken in to account in determining the optimum surface in terms of vision correction versus the quantity of corneal or lenticule material which needs to be removed. Similarly, where the corneal surface has an indentation in it which is relatively small in area and which would call for removing substantial corneal material over the rest of the cornea to correct the refraction in that small depression, it may be considered desirable to leave that small depression uncorrected. It will be understood that many considerations will go into the ophthalmologist's decision as to how to correct the measured refractive errors and that it is desirable to have the measurement system provide the ophthalmologist with alternative suggestions extending from the limit of safe material removal (if the refractive errors call for such a large correction) to lesser corrections which optimize other criteria such as material removal and so forth.

It will also be recognized that the ideal or optimum correction surface may have substantial local variations with the result that the correction is much more detailed than that provided by merely prism, cylindrical and spherical corrections. Such detailed correction may preferably be provided by the mask controlled laser shaping technique disclosed in related, incorporated by reference, U.S. patent application Ser. No. 07/402,946, entitled, "Laser Shaping With an Area Patterning Mask". Other techniques may also be used. Where it is considered desirable to do so, such as in situations where the correction will be done with eyeglasses or contact lenses, the prism, cylindrical and spherical portions of this correction may be extracted from this data and a new surface contour determined which will provide that correction. Further, for eyeglasses, the measured refractive error can be directly converted to diopters of correction required without knowledge of the existing contour of the cornea. Even in those situations where the correction will be done by shaping of the cornea or a lenticule, it may be desirable to derive prism, cylindrical and spherical corrections and compare them with the more detailed corrective surfaces as part of the process of selecting the actual corrective surface to be used.

Control system 180 may include these data reduction and contour determination functions or they may be separately performed on a different computer which is provided with both the refraction map of the eye and the contour of the cornea.

While the greatest benefit is obtained from the results of using this autorefractometer system by providing spatially resolved correction of the patient's vision or adjustment of the characteristics of other optical systems, it should be understood that prior art corrections which are limited to spherical, cylindrical and astigmatism can be derived from this data and applied in the prior art manner. Such use of this invention takes advantage of its short measurement time, but fails to make use of much of the information it can provide. Nevertheless, such use of the data is within the scope of the invention. Such low order correction information can be extracted from the spatially resolved refractive data by curve fitting procedures. Curve fitting procedures can be used in two dimensions with the fitting of a curve being done simultaneously with respect to the data along a number of different meridians of the eye. Alternatively, 3D or surface fitting techniques may be used as may any other appropriate techniques.

The term measurement surface has been loosely interchanged with the surface of the cornea. This introduces a slight error if the impingement orientation imposer or the position shifter (which ever is disposed conjugate to the cornea) is a plane, whereas, the cornea is curved. However, the distance between the collimating lens 114 or 214 and the cornea 142 or 242 on one hand and between the collimating lens 114 or 214 and the conjugate selector 130 or 220 on the other can be made large enough that any resulting measurement error is insignificant. Alternatively, the conjugate selector could be moved forward and back to maintain it at the same distance from collimating lens as the measurement point on the cornea.

While the preferred retina position detector in this embodiment is the quadrant detector 172, other detection techniques may be used. These include the use of a two dimensional array of light sensitive devices to determine the actual spot at which the bright spot is located. Other detectors, and other measurement techniques may also be employed for measuring the eye's refraction as a function of position along the surface of the cornea.

While the description of the use of the apparatus 108 of FIG. 4 and apparatus 208 of FIG. 9 has been in terms of measuring the refraction of the eye referenced to the surface of the cornea, it should be understood that the refraction measurement may be referenced to any desired location. In particular, if the measurements being taken are for the design of a contact lens, then it is preferred to place the measurement surface at the location where the surface of the contact lens will be by adjusting the position of the eye to place the expected position of the contact lens' surface at the conjugate location to the orientation or position selector. In this way, the refraction required at that surface in order to refract all rays extending parallel to the optical axis to the fovea centralis is determined directly and an appropriately shaped contact lens may be fabricated to provide that change in refraction. The measurement technique is similar where rather than a contact lens, a lenticule for essentially permanent attachment to the cornea is being fabricated. The measurement surface may also be made the location in which eyeglass lenses will be positioned in order to determine the correction which is appropriate for eyeglass lenses. Thus, the term "measurement surface" is used to refer to the surface (whether a physical interface between two different materials or an "imaginary" surface located at a specific location within one material such as air) at which the refractive characteristics are determined.

The non-subjective determination of the eye's refraction provided by this invention is desirable because it enables the refraction of an eye to be measured independent of the age, present mental capacity or state of consciousness of the patient and makes such measurement feasible from the time of birth on. It also makes measurement and correction of animal vision possible.

The discussion of the measurement process has been general. Normally, these measurements will be made on an uncorrected eye. However, they can also be made on an already corrected eye on which prior art correction has already been done, whether by corneal sculpturing (reshaping), attachment of a lenticule or by the presence of a contact lens. In these situations, the low order corrections (prism, cylindrical and spherical) have already been made (unless subsequent changes have taken place) and the system will be measuring data which relates to higher order terms only or to changes in those low order corrections. Once a correction based on such measurements has been determined, it can be applied to the cornea or lenticule, and if based on measurements with a contact lens in place, should have the contact lens correction included in it unless the patient desires to continue to wear the contact lens and have only the higher order corrections sculpted on the anterior surface of the eye. One reason for using a combination of a contact lens and sculptured correction would be where the low order corrections are large enough to raise concerns with respect to excessive thinning of the cornea if provided by corneal sculpturing. The higher order terms by themselves should not run that risk. Thus, a combination of corneal sculpturing and contact lens is appropriate for some patients.

While the discussion of the illustrated embodiments has concentrated on the measurement of the refractive characteristics of an eye because this system provides so many benefits over the prior art when used to measure an eye, it should be recognized that this measurement system can be used to measure any optical system with appropriate adaptation.

In optical systems where the image surface is a separate element of the system, the system for focusing an image of the image surface on a photodetector, such as the quadrant detector 172, may be omitted and the image detector itself may replace the image surface of the optical system during the measurement process. That is, the image surface does not have to be part of the optical system under test, but will be where the system under test is an eye. In other optical systems, the reference point from which displacement of a beam is determined or to which it is desired to deflect a beam will depend on the particular characteristics of the optical system. Thus, in some optical systems, there will be no equivalent to the fovea centralis or more than one equivalent.

While this measurement system may be used for any optical system, without restriction, it is more ideally suited to the measurement of an eye than to the measurement of a camera lens system. This is because the eye only accurately focuses the portion of the image which is within a few degrees of the optical axis and provides less accurate focus, or at least a less detailed mental image for portions of the image outside that small solid angle. Thus, the eye's refractive characteristics can be measured with sufficient accuracy by measuring them only for that small solid angle around the optic axis. In contrast, in a camera lens system, the entire image field of view is expected to be clearly focused on the film in order to provide a sharp picture of the entire field of view. Consequently, in order for this measurement system to determine the entire refractive characteristics of a camera lens system, measurements must be taken from many different positions of the measurement light source relative to the camera's lens system. While such measurements can be made to characterize such a lens system, such a lens system, unlike the eye, might be more efficiently tested by other test techniques.

The laser scanning systems of FIGS. 1, 4 and 9 are of general utility for other uses than testing optical systems. Their ability to independently control beam position and beam orientation at a surface has utility in many areas. For example, these systems can be used for optically addressing different devices, with the beam position selecting one group of devices out of a plurality of groups and the beam orientation selecting an individual member of the selected group, where the devices are positioned relative to a conjugate surface in a manner which causes them to be illuminated one at a time as a function of the angle of incidence. For example, positioning them a distance from the conjugate plane or having fiber optic cables disposed at different orientations and other techniques may be used.

Information about the eye's refractive characteristics can also be obtained, in an objective system, by using a measurement beam which is always parallel to the optical axis in combination with a photodetector which provides output signals which facilitate determination of the location of the bright spot on the retina. The photodetector may be an X-Y array of photosensitive cells such as a charge coupled device imager. While such a technique enables the present refractive errors of the eye to be determined, at the present time it requires much more time to determine the location of the image of the beam than is required in the preferred embodiments to move the beam to the reference point. It is for this reason that such a system is not preferred. Such a system may be provided by substituting an array detector for the quadrant detector either in system 108 or system 208 and either omitting the orientation imposer or by controlling the orientation imposer in the system to retain the measurement beam parallel to the optical axis.

While determination of proper refraction for an image position at infinite distance is most easily performed, the system may also be employed to perform a refraction for an image which is substantially closer to the eye. In so doing, the fixation point is moved to the desired image distance and the refraction is performed in the same manner as has been described.

In general, the data obtained can be preserved in any of a variety of ways. These including storing it in a computer or other control system, printing it out in a permanent hardcopy form, displaying it for an operator to write down, further processing it into control data for use in generating a corrective lens or lenticule or for use in modifying the existing surface of the cornea to provide improved vision or any of a wide variety of other techniques. All such techniques fall in the general class of storing, recording or preserving the data for a sufficient period of time to enable the measured refraction data to be put to therapeutic or diagnostic use. We use the word "storing" as a general term which encompasses such preservation of the data thus obtained, no matter how that storage is performed.

While the invention has been described in detail herein in accord with certain embodiments thereof, many modifications and changes therein may be effected by those skilled in the art. Accordingly, it is intended by the appended claims to cover all such modifications and changes as fall within the true spirit and scope of the invention.

What is claimed is:

1. A refractometer comprising:
   means for providing a reference pattern to be viewed by an eye whose refraction is to be measured wherein said reference pattern comprises an annulus;
   means for providing a measurement pattern to the eye wherein said measurement pattern comprises a disk-like pattern, said means for providing a measurement pattern being positioned adjacent to said means for providing a reference pattern;
   means, connected to said means for providing a measurement pattern, for adjusting said means for providing a measurement pattern to change a position and/or orientation of said measurement pattern in order to enable a patient to use the eye to perceive said measurement pattern in a desired relationship to said reference pattern; and
   means for storing data representative of the position and/or orientation of said measurement pattern when said measurement pattern is in said desired relationship to said reference pattern, said data being indicative of refraction characteristics of the eye.

2. A method for determining the characteristics of an eye comprising:
   (a) providing a reference pattern to said eye;
   (b) directing a measuring beam of light into said eye, said beam passing through a measurement point on an anterior surface of said eye and being narrower in cross-section than the entrance aperture of said eye;
   (c) sensing an offset between a reference point on the retina and a location at which said beam impinges on the retina;
   (d) changing the orientation at which said beam impinges on said anterior surface at said measurement point to an orientation for which said beam impinges on said retina at said reference point;
   (e) storing, for each measuring point, the orientation in step (d) for which said beam impinges on said retina at said reference point;
   (f) storing the location of each measurement point in association with said orientation;
   (g) repeating said method for at least three measurement points on said anterior surface of said eye;
   (h) determining the refractive characteristics of said eye from the measured orientations for which said beam impinges on the retina at the reference point; and
   (i) determining a spatially resolved refraction from said refractive characteristics.

3. The method recited in claim 2 wherein step (d) comprises:
   feeding back a signal representative of the sensed direction from said reference point to the location where said beam impinges on said retina, said feedback being to a control system which controls the orientation of said beam and, said feedback signal having a polarity to drive said impingement-on-the-retina point to said reference point in a self-centering manner.

4. The method recited in claim 3 further comprising the step of:
   determining the refractive characteristics of said eye at said measurement point from the measured orientation for which said beam, when disposed at said measurement point, impinges on the retina at said reference point.

5. The method recited in claim 2 wherein said step of changing said orientation comprises:
   the patient whose eye is being examined controlling the orientation of said measurement beam at said measurement point to bring the image of the measurement beam into a predetermined relationship with respect to a reference pattern.

6. A method for determining vision correction parameters for an eye comprising:
   (a) directing a beam of light into said eye, said beam passing through a measurement point on the anterior surface of said eye, said beam being narrower in cross-section than the entrance aperture of said eye;
   (b) sensing an offset between a reference point on the retina of said eye and a location where said beam impinges on said retina;
   (c) while keeping said beam directed at said measurement point, changing the orientation of said beam relative to the optical axis of said eye to an orientation which shifts the location of said beam's impingement point on said retina toward said reference point wherein said beam impinges on said retina at said reference point;
   (d) storing, for each measurement point on said anterior surface, the relative orientation for which said beam impinges on said retina at said reference point, said stored relative orientation being dependent on the refractive characteristics of the eye;
   (e) determining from said orientation data, a first point on said anterior surface where minimal correction is required; and
   (f) determining for all other points on said anterior surface the degree of correction required relative to said first point.

7. The method recited in claim 6 further comprising the step of:

determining a detailed pattern for shaping an optical surface located substantially at said anterior surface to provide correction for said eye, said optical surface being selected from the group comprising: a surface of a cornea of said eye, a surface of a contact lens, and a surface of a lenticule.

8. The method recited in claim 6 further comprising: extracting a spherical correction from said refractive characteristics.

9. The method recited in claim 8 further comprising: extracting a cylindrical correction from said refractive characteristics.

10. The method recited in claim 9 further comprising: extracting from said refractive characteristics a correction which is more detailed than cylindrical and spherical corrections.

11. The method recited in claim 6 further comprising: extracting from said refractive characteristics a correction which is more detailed than cylindrical and spherical corrections.

12. The refractometer for measuring the deviation of the refractive characteristics of an eye having a retina and a cornea from a desired optical performance of said eye comprising:
means for providing a reference beam of light which forms a first image of a reference pattern on said retina after passing through a first point on said cornea;
means for directing a second beam of light into said eye with a separately controllable position and angular orientation at said cornea, said second beam forming a second image on said retina, said reference beam and said second beam having diameters at said cornea which are substantially smaller than a predetermined size of an entrance aperture of said eye;
means for sensing an alignment of said second image with respect to said first image;
means for altering said angular orientation of said second beam in order to produce an alignment of said second image with respect to said first image that is substantially indicative of said desired optical performance of said eye;
means for storing said indicative orientation of said second image with respect to said first image; and
means for providing a spatially resolved map of said refractive characteristics of said eye by operating said means for directing said second beam over a plurality of predetermined measurement regions on an anterior surface of said eye.

13. The refractometer, recited in claim 12, wherein: said means for altering said angular orientation comprises:
a control system to which said means for directing is responsive.

14. The refractometer as recited in claim 12, wherein said sensing means is further comprised of:
an electronic image sensing means viewing said first and second images on said retina through said eye; and an image processing system which determines said alignment of said first and second images.

15. The refractometer recited in claim 12 wherein: said means for providing a reference beam comprises;
a source of the projected second light beam;
a collimating lens disposed in the path of said second beam;
means for imposing an impingement orientation on said second beam, said means for imposing being disposed in the path of said second beam between said light source and said collimating lens;
means for positioning said second beam at selected measurement points, said means for positioning being disposed in the path of said second beam between said light source and said collimating lens; and
said sensing portion which is comprised of:
a transducer for converting sensed light to an electrical signal, and
means for imaging said retina onto said transducer.

16. The refractometer recited in claim 15 wherein: said means for positioning is disposed between said means for imposing and said collimating lens.

17. The refractometer recited in claim 15 wherein: said means for positioning and said collimating lens are positioned such that said means for positioning is at a conjugate position with respect to an intended position of said anterior surface of said eye during said measurement.

18. The refractometer recited in claim 15 wherein: said means for positioning comprises:
means for scanning.

19. The refractometer recited in claim 17 wherein: said means for positioning comprises means:
for scanning said second beam along said anterior surface of said eye in a random access manner.

20. The refractometer recited in claim 19 wherein: said means for positioning comprises:
a scanning mirror.

21. The refractometer recited in claim 18 wherein said means for scanning comprises:
a movable opaque member having a transmissive portion.

22. The refractometer recited in claim 21 wherein said transmissive portion of said movable opaque member comprises:
an aperture in said member.

23. The refractometer recited in claim 15 wherein: said means for imposing comprises:
a two-dimensional acoustic/optical scanner.

24. The refractometer recited in claim 15 wherein: said means for positioning is disposed substantially at the focal plane of said collimating lens.

25. The refractometer recited in claim 24 wherein: said means for positioning comprises:
a scanning mirror.

26. The refractometer recited in claim 25 wherein: said means for imposing is disposed at a conjugate location to said eye with respect to said collimating lens.

27. The refractometer recited in claim 26 wherein: said means for imposing comprises:
a two-dimensional acoustic/optical scanner.

28. The refractometer recited in claim 26 wherein said sensing portion comprises:
means for deflecting light emerging from said eye away from the optical axis of said projecting portion; and
means for focusing light, which is deflected by said means for deflecting, onto said transducer as an image of said retina.

29. The refractometer recited in claim 28 wherein: said means for deflecting comprises:
a beam splitter which is disposed in the path of said second light beam between said source and an intended position of said eye during measurement.

30. The refractometer recited in claim 29 wherein:

said means for deflecting is disposed between said collimating lens and the position of the eye during said measurement.

31. The refractometer recited in claim 29 wherein:
said beam splitter is a polarizing beam splitter and said second beam is polarized in a pass orientation of said beam splitter.

32. The refractometer recited in claim 28 wherein:
said transducer comprises:
a quadrant detector.

33. The refractometer recited in claim 32 further comprising a control means connected to receive an output of said quadrant detector and to control said means for imposing an impingement orientation and to keep said second beam centered in said quadrant detector as the measurement point is scanned along the anterior surface of said eye.

34. The refractometer recited in claim 33 wherein:
said control means is configured to, in response to a sensed second beam location on the retina which is away from said reference point, to cause said means for imposing to impose a new impingement orientation which is changed in a direction to move the sensed location of said second beam on the retina toward the reference point.

35. The refractometer recited in claim 33 further comprising:

means for relating the impingement angles which placed the sensed position of said second beam at the reference point on the retina to change in the shape of said anterior surface which will cause the eye to exhibit more desirable refraction.

36. A refractometer comprising:
means for providing a reference pattern to be viewed by an eye whose refraction is to be measured wherein said reference pattern comprises an annulus;
means for providing a measurement pattern to the eye wherein said measurement pattern comprises a disk-like pattern, said means for providing a measurement pattern being positioned adjacent to said means for providing a reference pattern;
means, connected to said means for providing a measurement pattern, for adjusting said means for providing a measurement pattern to change a position and/or orientation of said measurement pattern in order to enable a patient to use the eye to perceive said measurement pattern in a desired relationship to said reference pattern; and
means for providing data indicative of refraction characteristics of the eye and based upon adjustments made to the means for providing a measurement pattern in order to bring said measurement pattern into said desired relationship to said reference pattern.

* * * * *